(12) United States Patent
Angelescu

(10) Patent No.: US 9,389,158 B2
(45) Date of Patent: Jul. 12, 2016

(54) PASSIVE MICRO-VESSEL AND SENSOR

(71) Applicant: Dan Angelescu, Le Perreux sur Marne (FR)

(72) Inventor: Dan Angelescu, Le Perreux sur Marne (FR)

(*) Notice: Subject to any disclaimer, the term of this patent is extended or adjusted under 35 U.S.C. 154(b) by 574 days.

(21) Appl. No.: 13/760,879

(22) Filed: Feb. 6, 2013

(65) Prior Publication Data

US 2013/0269423 A1    Oct. 17, 2013

Related U.S. Application Data

(63) Continuation-in-part of application No. 13/025,467, filed on Feb. 11, 2011, now Pat. No. 8,506,907.

(60) Provisional application No. 61/337,998, filed on Feb. 12, 2010.

(51) Int. Cl.
| | |
|---|---|
| *G01N 11/02* | (2006.01) |
| *G01N 1/10* | (2006.01) |
| *E21B 47/02* | (2006.01) |
| *E21B 47/10* | (2012.01) |
| *E21B 49/08* | (2006.01) |

(Continued)

(52) U.S. Cl.
CPC ............. *G01N 11/02* (2013.01); *A61B 5/1468* (2013.01); *A61M 5/14248* (2013.01); *A61M 5/14276* (2013.01); *E21B 47/02* (2013.01); *E21B 47/1015* (2013.01); *E21B 49/081* (2013.01); *G01N 1/10* (2013.01); *A61B 5/1427* (2013.01); *A61B 5/1455* (2013.01); *A61B 5/14735* (2013.01); *A61B 5/155* (2013.01); *A61B 2562/028* (2013.01); *A61M 2005/14513* (2013.01)

(58) Field of Classification Search
CPC ... E21B 47/02; E21B 47/1015; E21B 47/081; A61M 5/14276; A61M 5/14248; A61M 5/14513; G01N 11/02; G01N 1/10; A61B 5/1468; A61B 5/1472; A61B 5/155; A61B 5/1455; A61B 5/14735; A61B 2562/028
See application file for complete search history.

(56) References Cited

U.S. PATENT DOCUMENTS

| | | | |
|---|---|---|---|
| 1,909,205 A | 5/1933 | McCollum | 367/58 |
| 3,399,727 A | 9/1968 | Graham et al. | 166/42 |

(Continued)

FOREIGN PATENT DOCUMENTS

| | | |
|---|---|---|
| EP | 0620893 B1 | 12/2000 |
| EP | 1137862 B1 | 3/2004 |

(Continued)

OTHER PUBLICATIONS

European Patent Office, International Preliminary Report on Patentability-International Application No. PCT/EP2014/052350 dated May 5, 2015, 6 pages.

(Continued)

*Primary Examiner* — J. Christopher Ball
(74) *Attorney, Agent, or Firm* — Sunstein Kann Murphy & Timbers LLP

(57) ABSTRACT

An electrically passive device and method for in-situ acoustic emission, and/or releasing, sampling and/or measuring of a fluid or various material(s) is provided. The device may provide a robust timing mechanism to release, sample and/or perform measurements on a predefined schedule, and, in various embodiments, emits an acoustic signal sequence(s) that may be used for triangulation of the device position within, for example, a hydrocarbon reservoir or a living body.

56 Claims, 26 Drawing Sheets

(51) Int. Cl.
*A61M 5/142* (2006.01)
*A61B 5/1468* (2006.01)
*A61B 5/155* (2006.01)
*A61M 5/145* (2006.01)
*A61B 5/1455* (2006.01)
*A61B 5/1473* (2006.01)

(56) References Cited

U.S. PATENT DOCUMENTS

| | | | |
|---|---|---|---|
| 3,766,733 A | 10/1973 | Drzewiecki et al. | 60/36 |
| 4,057,780 A | 11/1977 | Shuck | 340/15.5 MC |
| 4,547,468 A | 10/1985 | Jones et al. | 501/33 |
| 4,791,251 A | 12/1988 | Carter et al. | 200/33 R |
| 4,893,505 A | 1/1990 | Marsden et al. | 73/155 |
| 5,441,110 A | 8/1995 | Scott, III | 166/308 |
| 5,503,225 A | 4/1996 | Withers | 166/250.1 |
| 6,443,228 B1 | 9/2002 | Aronstam et al. | 166/250.11 |
| 6,619,311 B2 | 9/2003 | O'Connor et al. | 137/109 |
| 6,891,477 B2 | 5/2005 | Aronstam | 340/606 |
| 6,898,529 B2 | 5/2005 | Gao et al. | 702/11 |
| 7,082,993 B2 | 8/2006 | Ayoub et al. | 166/250.1 |
| 7,134,492 B2 | 11/2006 | Willberg et al. | 166/250.1 |
| 7,216,533 B2 | 5/2007 | McGregor et al. | 73/152.27 |
| 7,318,912 B2 | 1/2008 | Pezzuto et al. | 422/103 |
| 7,455,667 B2 | 11/2008 | Uhland et al. | 604/890.1 |
| 7,712,527 B2 | 5/2010 | Roddy | 166/250.14 |
| 8,129,318 B2 | 3/2012 | McDaniel et al. | 507/271 |
| 8,506,907 B2 | 8/2013 | Angelescu | 422/550 |
| 2003/0104590 A1 | 6/2003 | Santini, Jr. et al. | 435/174 |
| 2007/0048192 A1 | 3/2007 | Kartalov et al. | 422/100 |
| 2008/0047836 A1 | 2/2008 | Strand et al. | 204/644 |
| 2009/0126996 A1 | 5/2009 | Villareal et al. | 175/50 |
| 2009/0288820 A1 | 11/2009 | Barron et al. | 166/249 |
| 2010/0051266 A1 | 3/2010 | Roddy et al. | 166/250.01 |
| 2011/0186290 A1 | 8/2011 | Roddy et al. | 166/253.1 |
| 2011/0198221 A1 | 8/2011 | Angelescu | 204/400 |
| 2012/0037368 A1 | 2/2012 | Eick et al. | 166/300 |
| 2012/0048538 A1 | 3/2012 | Brannon | 166/250.01 |

FOREIGN PATENT DOCUMENTS

| | | | |
|---|---|---|---|
| FR | 2253409 | 6/1975 | G01N 11/06 |
| GB | 2443900 A | 5/2008 | |
| GB | 2459793 A | 11/2009 | |
| WO | WO 2011/100509 A2 | 8/2011 | |

OTHER PUBLICATIONS

Angelescu, "Highly Integrated Microfluidics Design", Artech House, Inc., Norwood, MA, 2011.
Beeby et al., "MEMS Mechanical Sensors", Artech House, Inc., Norwood, MA, 2004.
Grayson, A.C.R. et al., "Multi-pulse drug delivery from a resorbable polymeric microchip device", Nature Materials, vol. 2, pp. 767-772 + supplemental information, Nov. 2003.
International Searching Authority, International Search Report—International Application No. PCT/US2011/024467, together with the Written Opinion of the International Searching Authority, 8 pages, Sep. 23, 2011.
International Searching Authority, International Search Report—International Application No. PCT/EP2014/052350 together with the Written Opinion of the International Searching Authority, 10 pages, May 20, 2014.
Miller et al., "Fracturing Oil Shale with Explosives for in Situ Recovery", Am. Chem. Soc. 167$^{th}$ Nat'l Mtg, Los Angeles—Symposium on Shale Oil, Tar Sands and Related Fuel Sources, pp. 60-85, Mar. 31-Apr. 5, 1974.
Montgomery et al., "Hydraulic Fracturing—History of an Enduring Technology", Journal of Petroleum Technology, pp. 26-41, Dec. 2010.
Oh et al., "Topical review: A review of microvalves", J. Micromechanics and Microengineering, vol. 16, pp. R13-R39, 2006.
Prescott et al., "Chronic, programmed polypeptide delivery from an implanted, multireservoir microchip device", Nature Biotechnology, vol. 24, No. 4, pp. 437-438, Apr. 2006.
Santini, Jr. et al., "Microchips as Controlled Drug-Delivery BUDevices", Angewandte Chemie International EdiBVtion, vol. 39, pp. 2396-2407, 2000.
Staples et al., "Application of Micro- and Nano-Electromechanical Devices to Drug Delivery", Pharmaceutical Research, vol. 23, No. 5, May 2006.
Stone et al., "Engineering Flows in Small Devices: Microfluidics Toward a Lab-on-a-Chip", Annual Review of Fluid Mechanics, vol. 36, pp. 381-411, 2004.
Vogel et al., "Optical and acoustic investigations of the dynamics of laser-produced cavitation bubbles near a solid boundary", Journal of Fluid Mechanics, vol. 206, pp. 299-338, 1989.

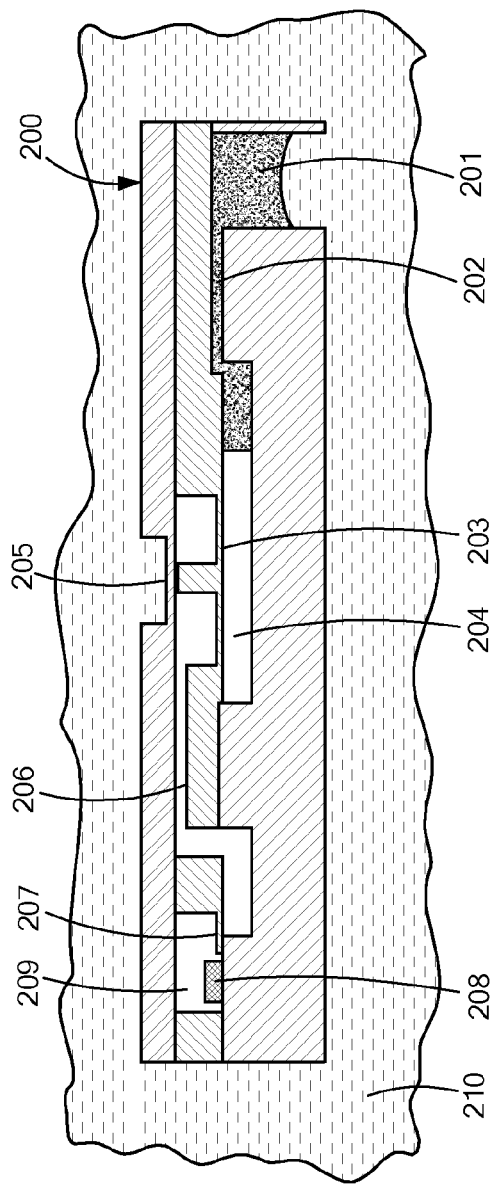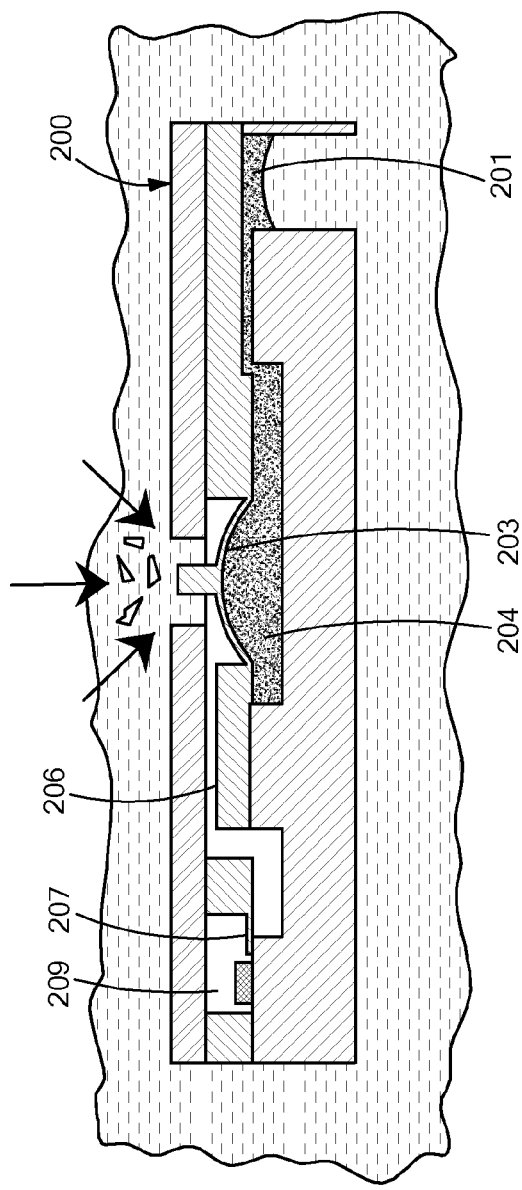
FIG. 2(a)
FIG. 2(b)

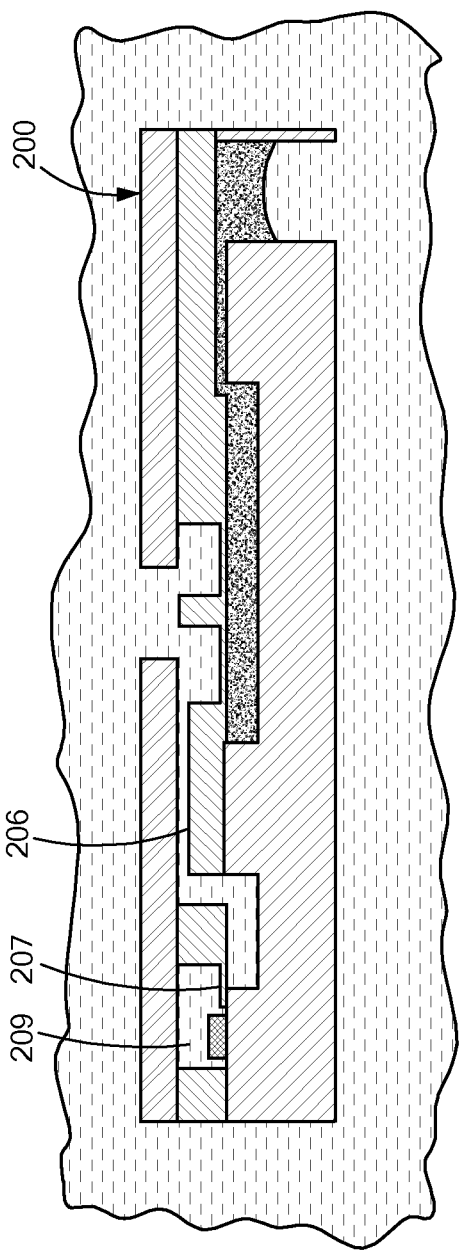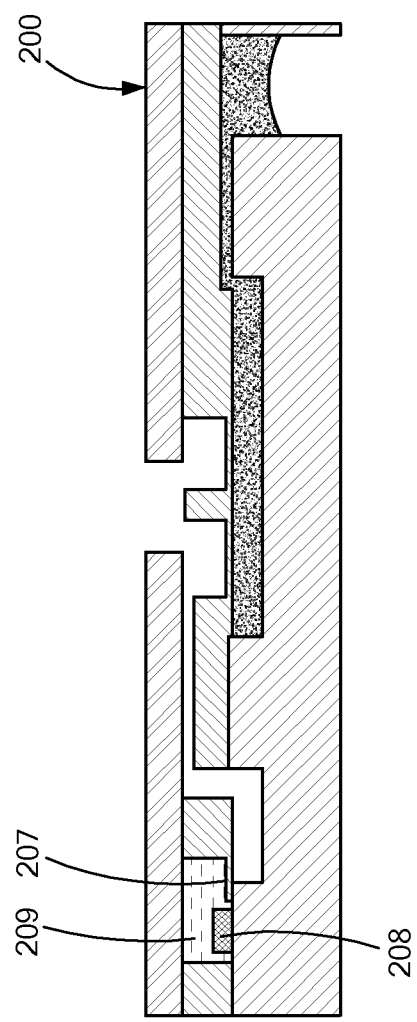

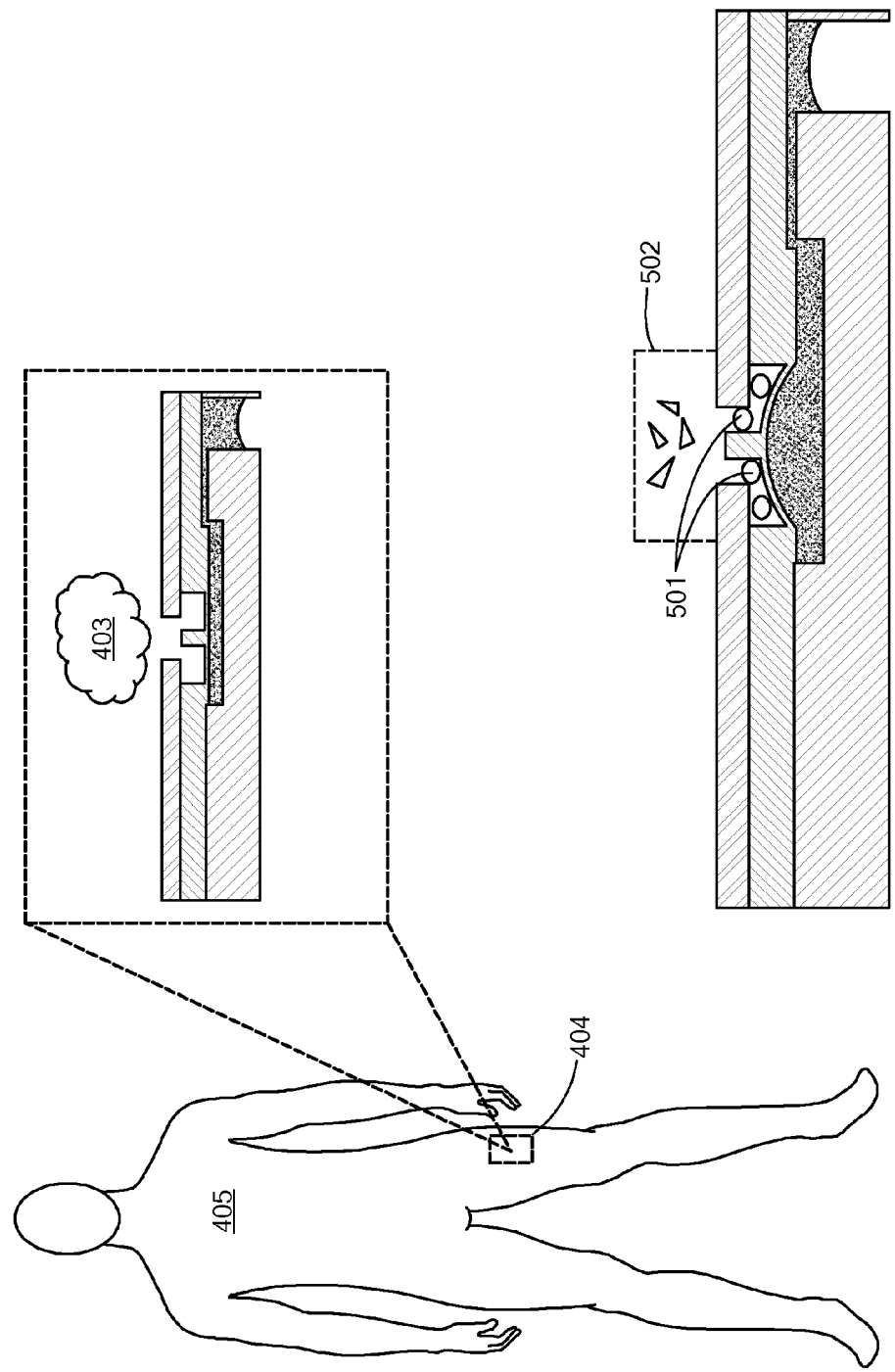

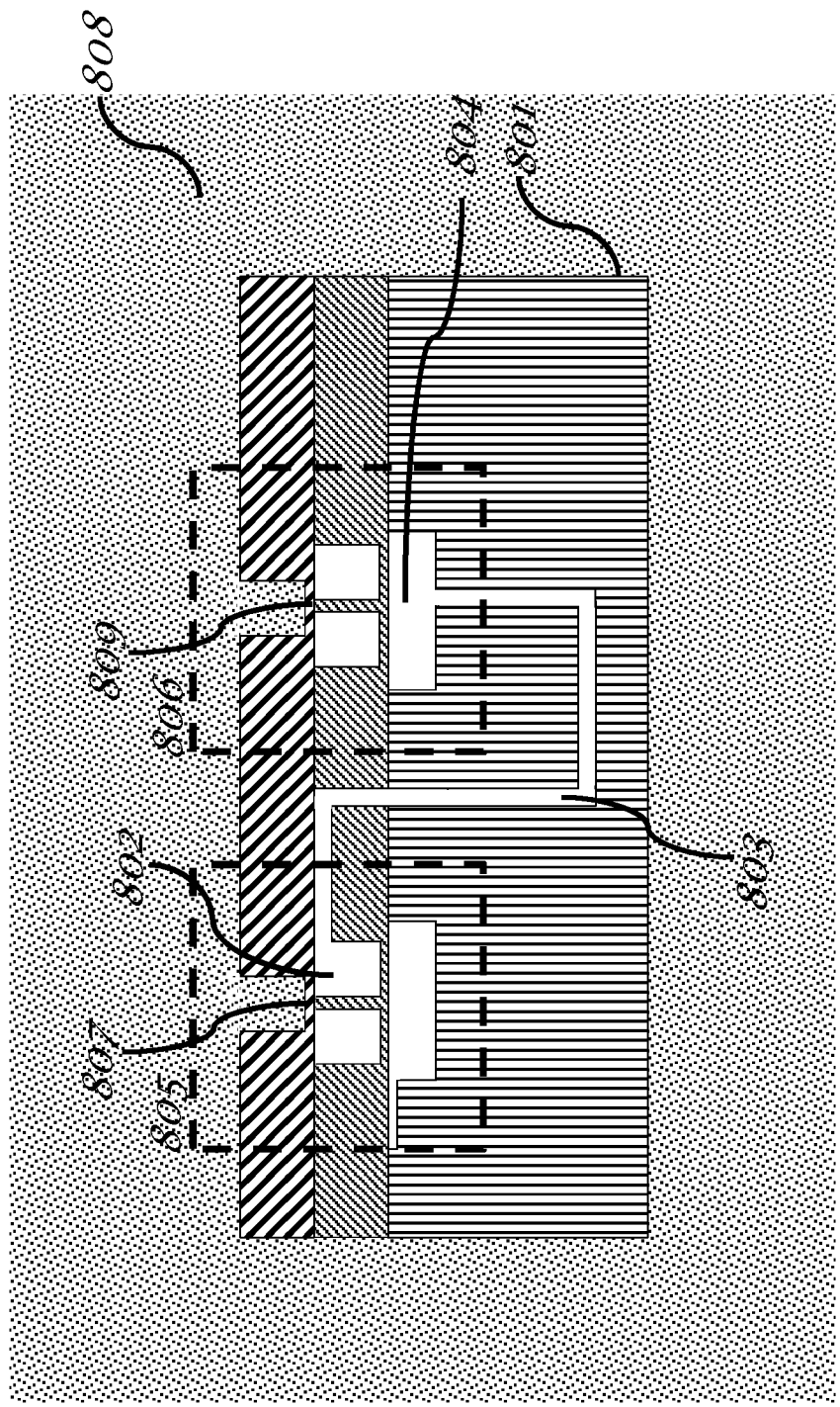
Fig. 8-A

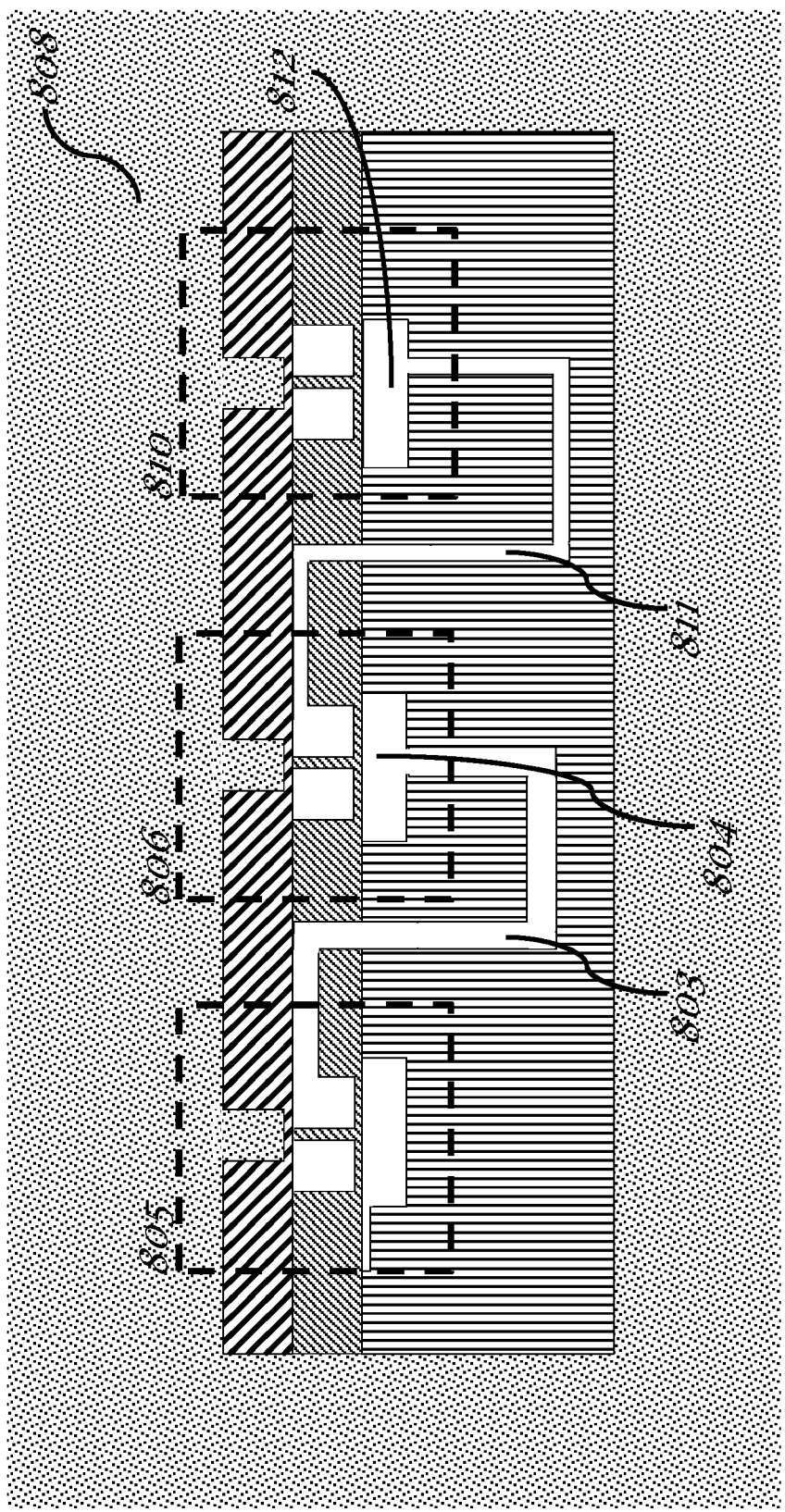
Fig. 8-B

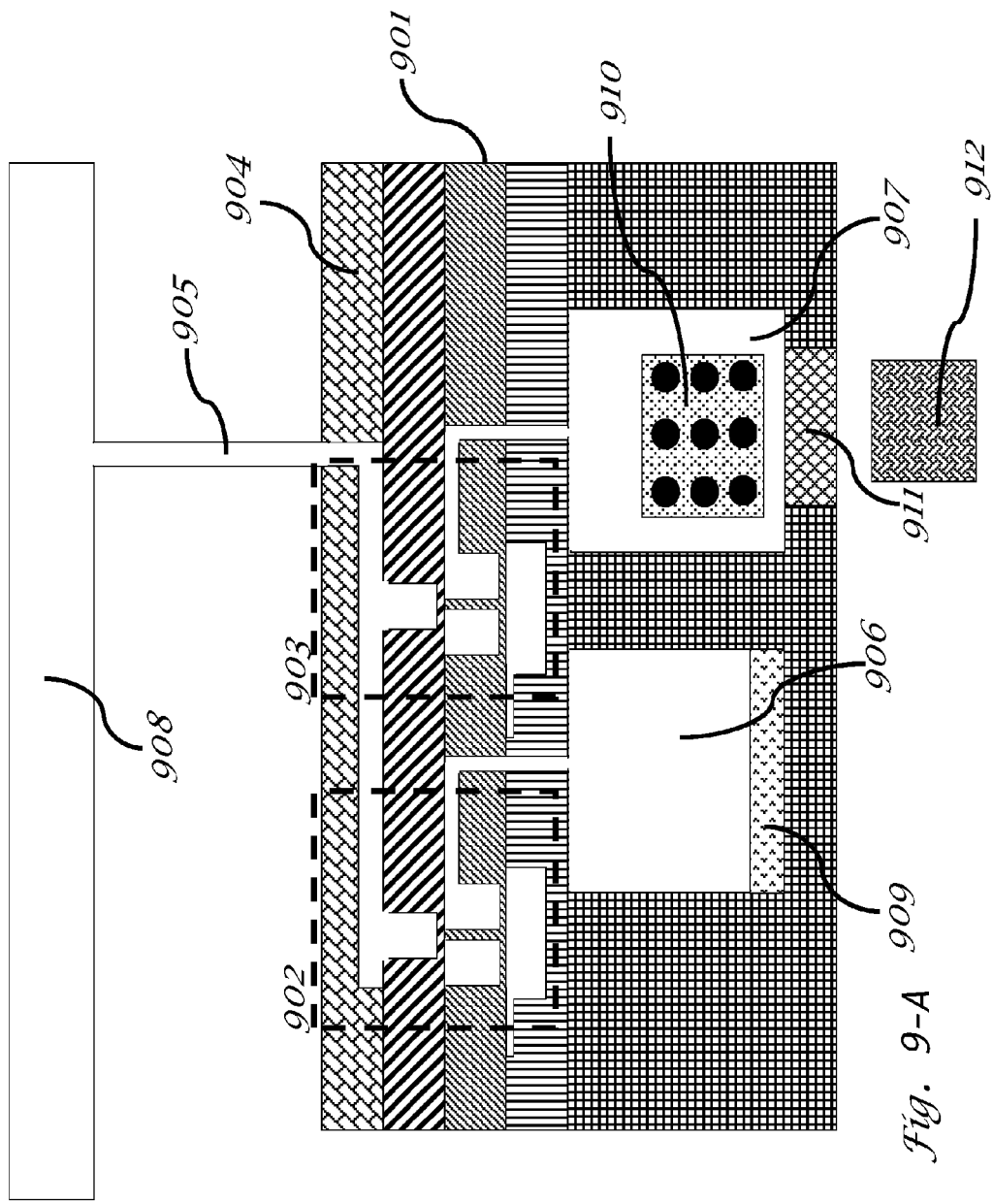
Fig. 9-A

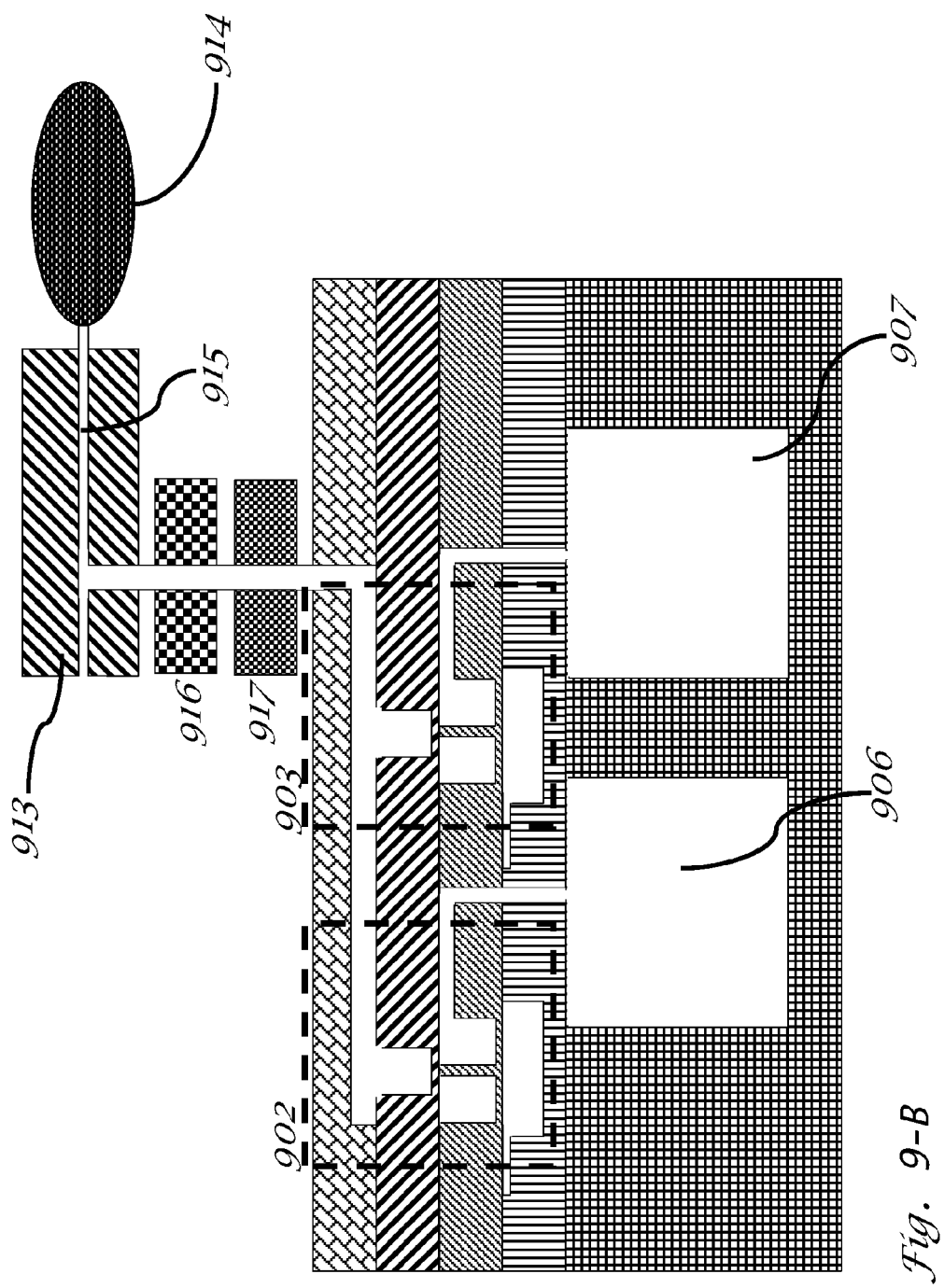
Fig. 9-B

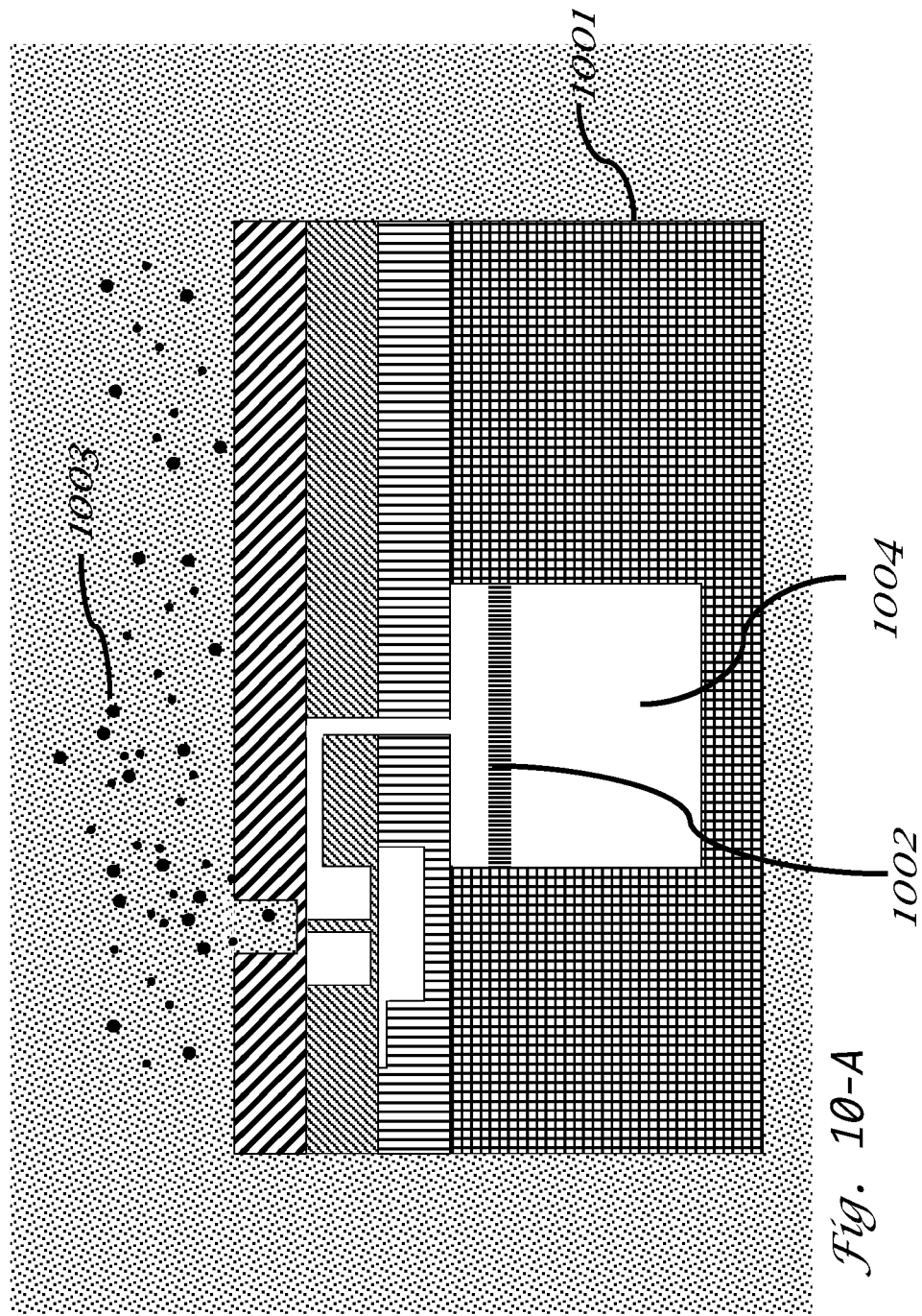
Fig. 10-A

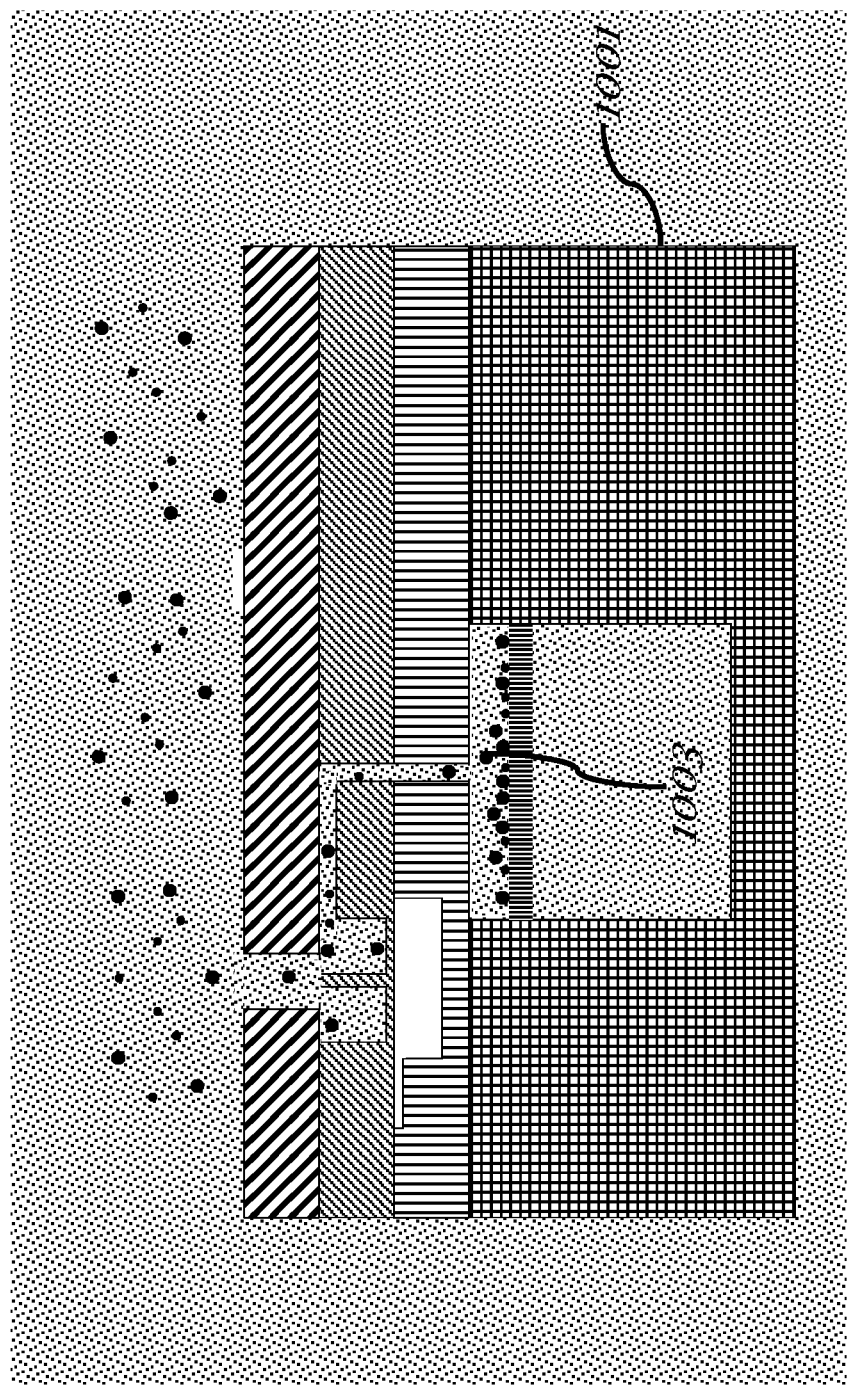
Fig. 10-B

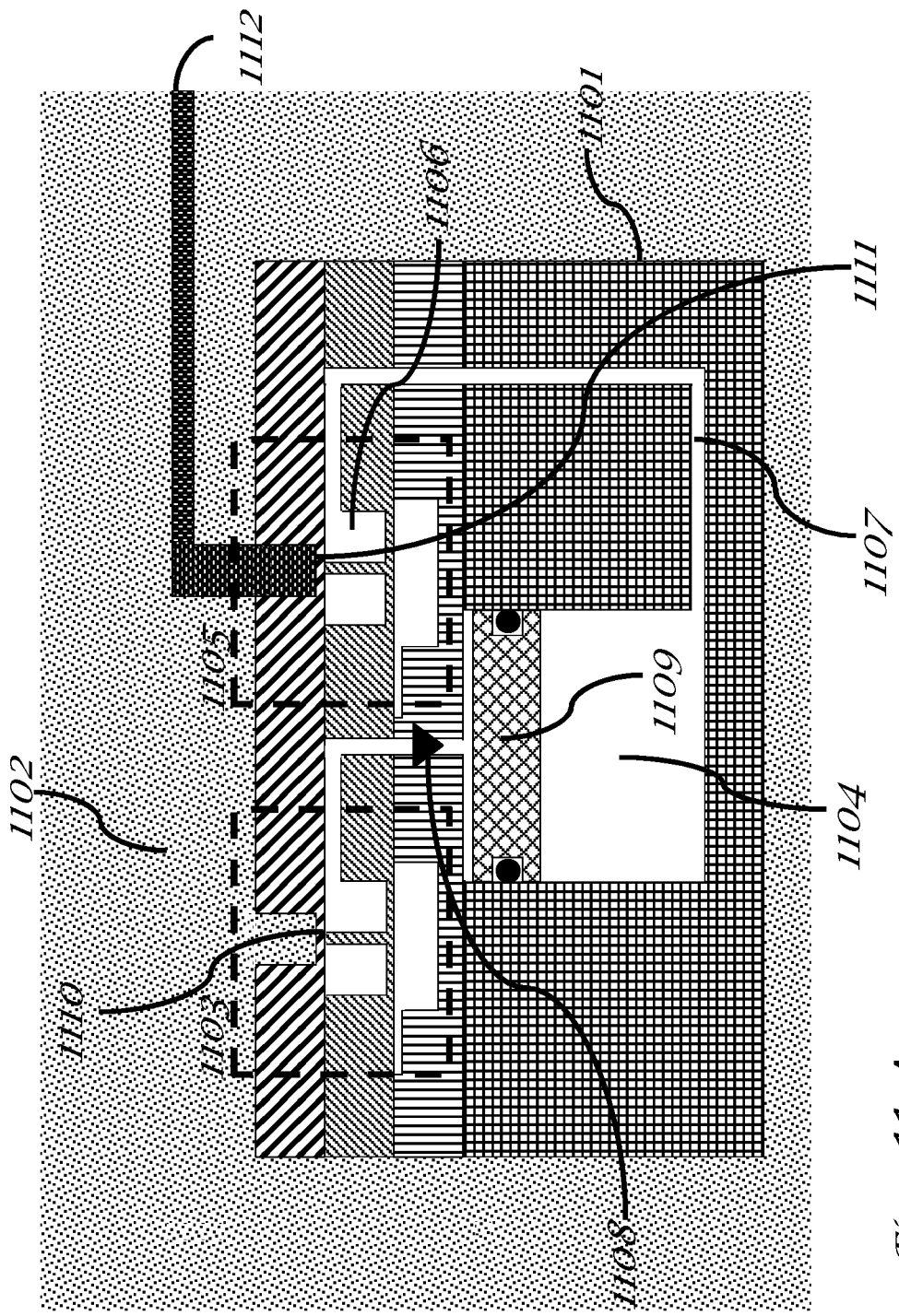
Fig. 11-A

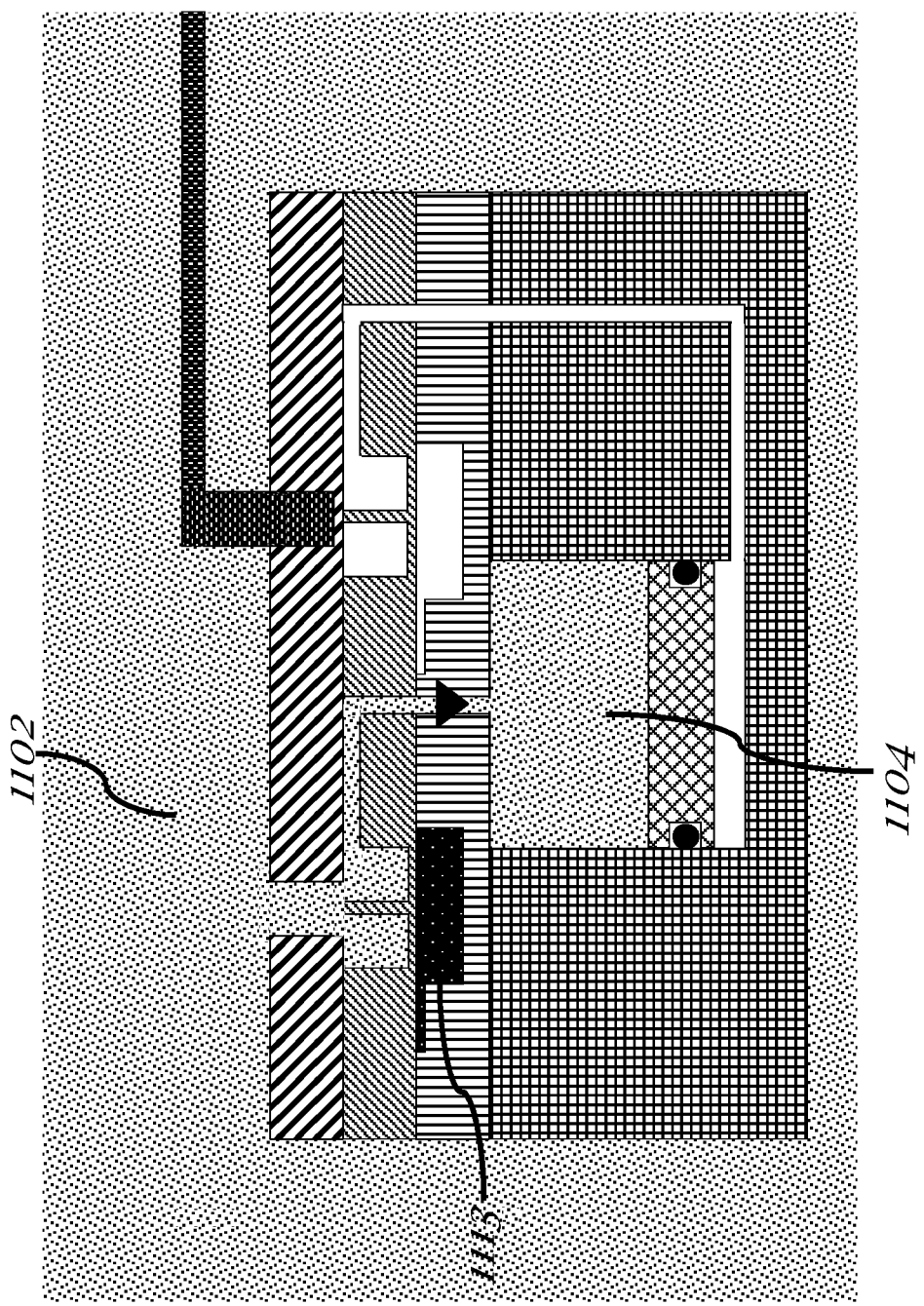
Fig. 11-B

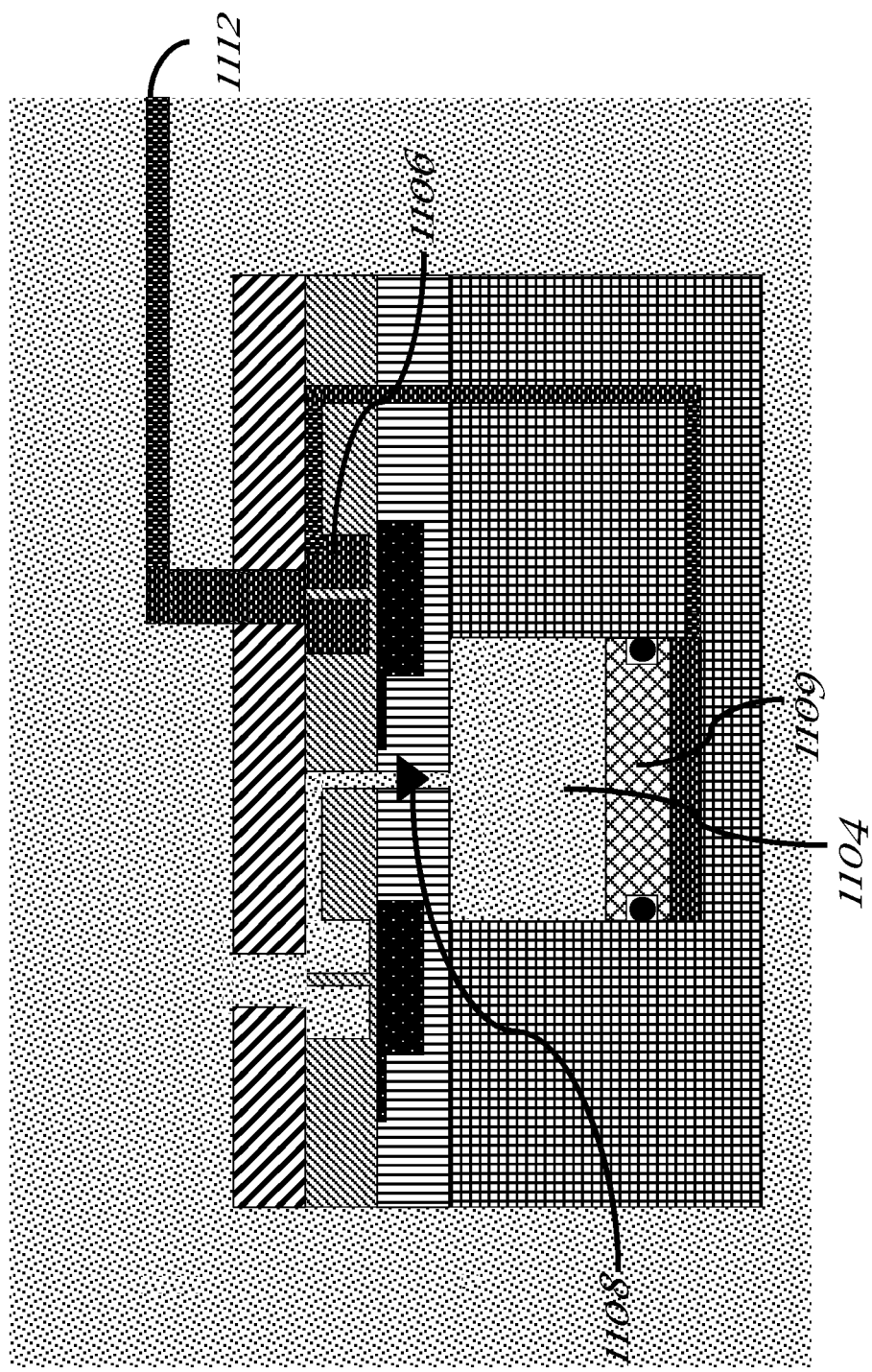
Fig. 11-C

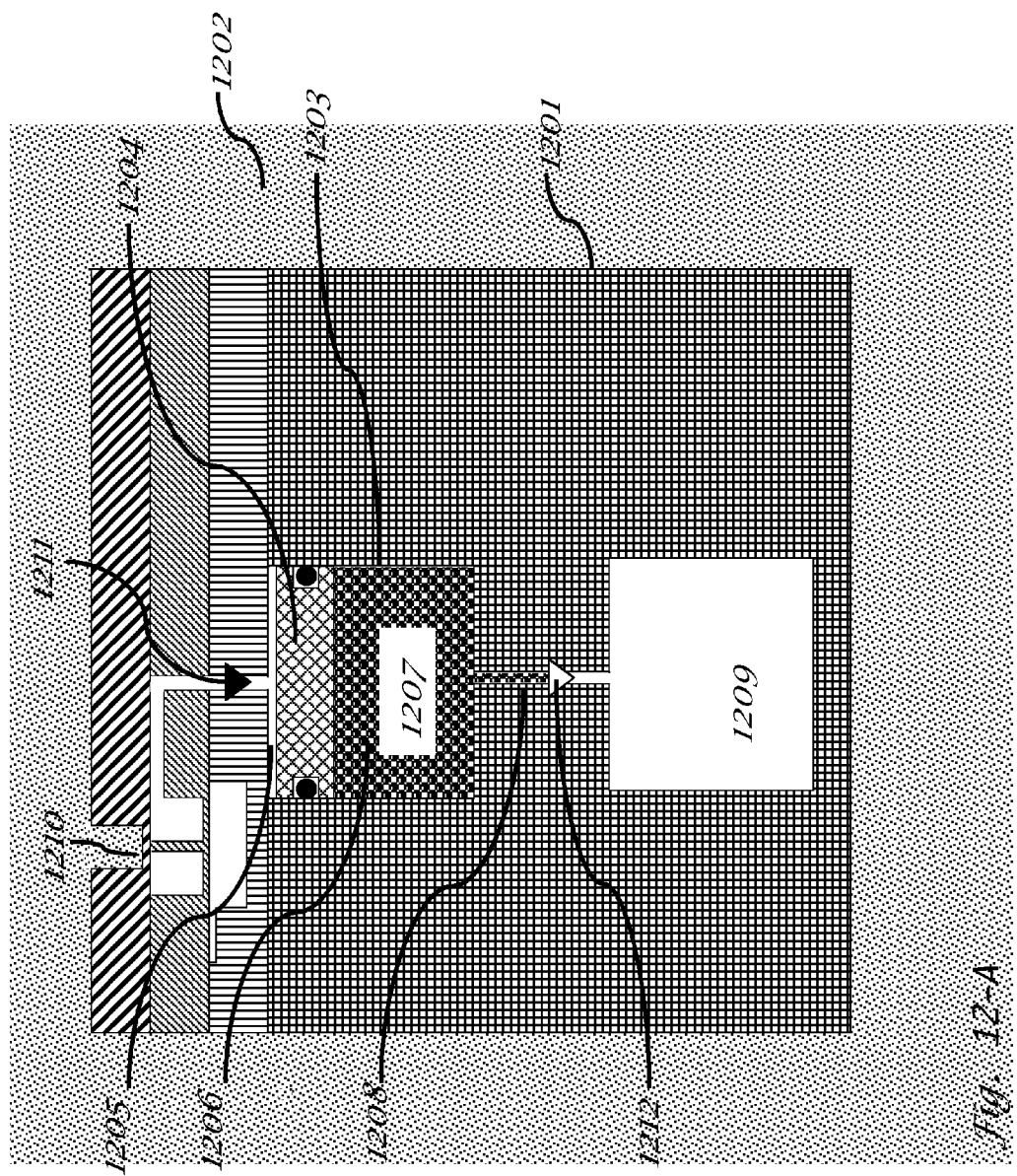

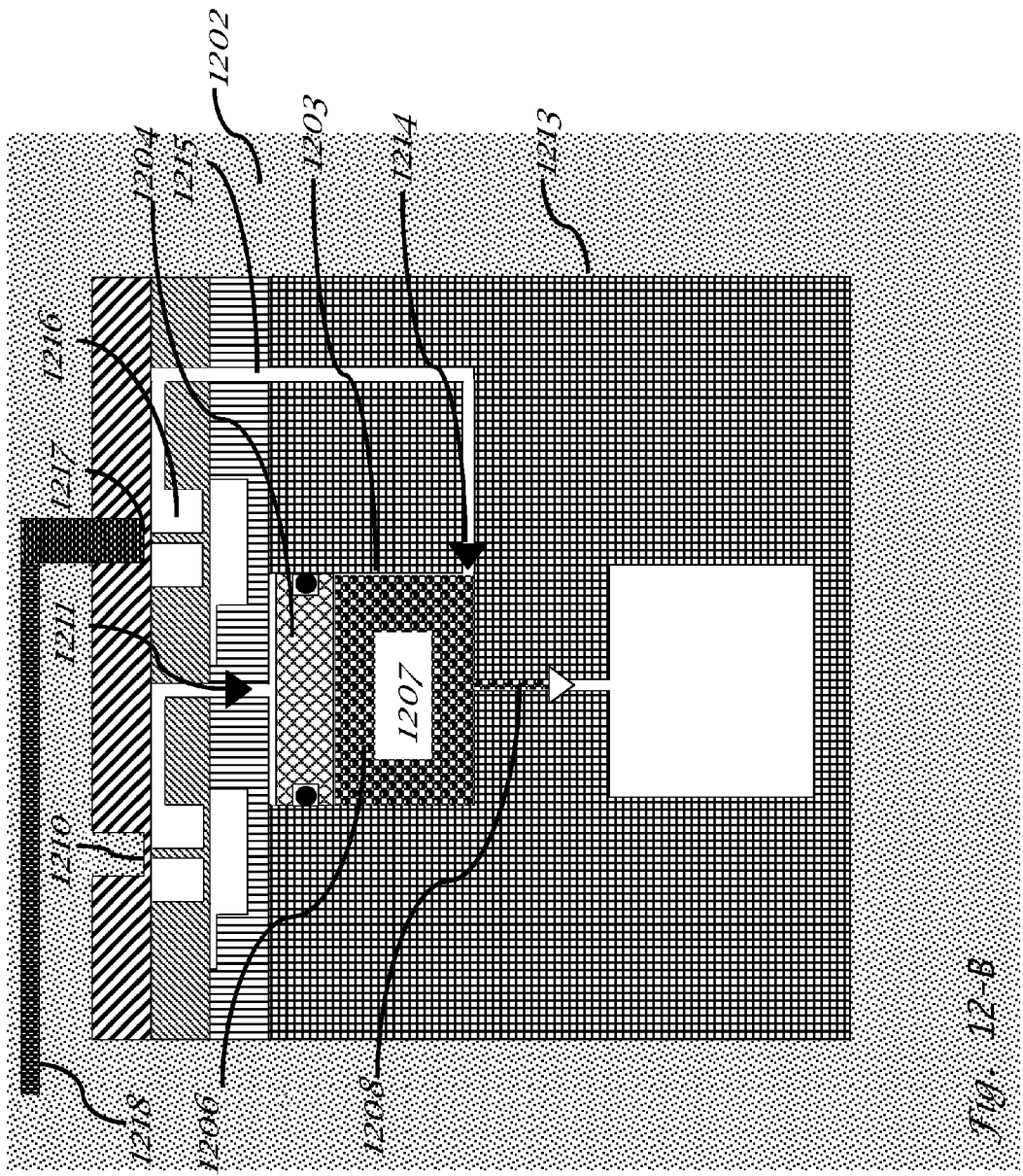

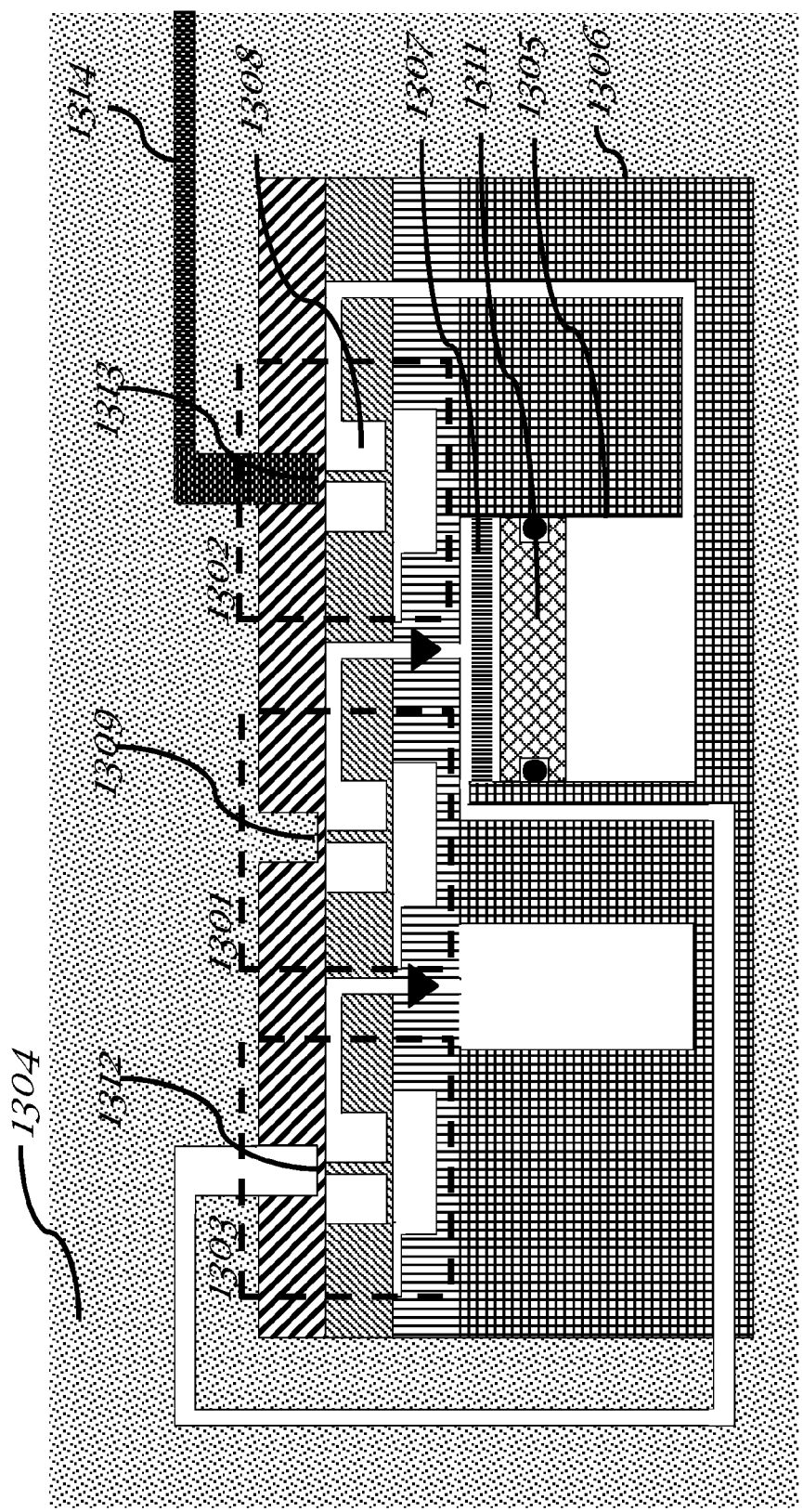
Fig. 13-A

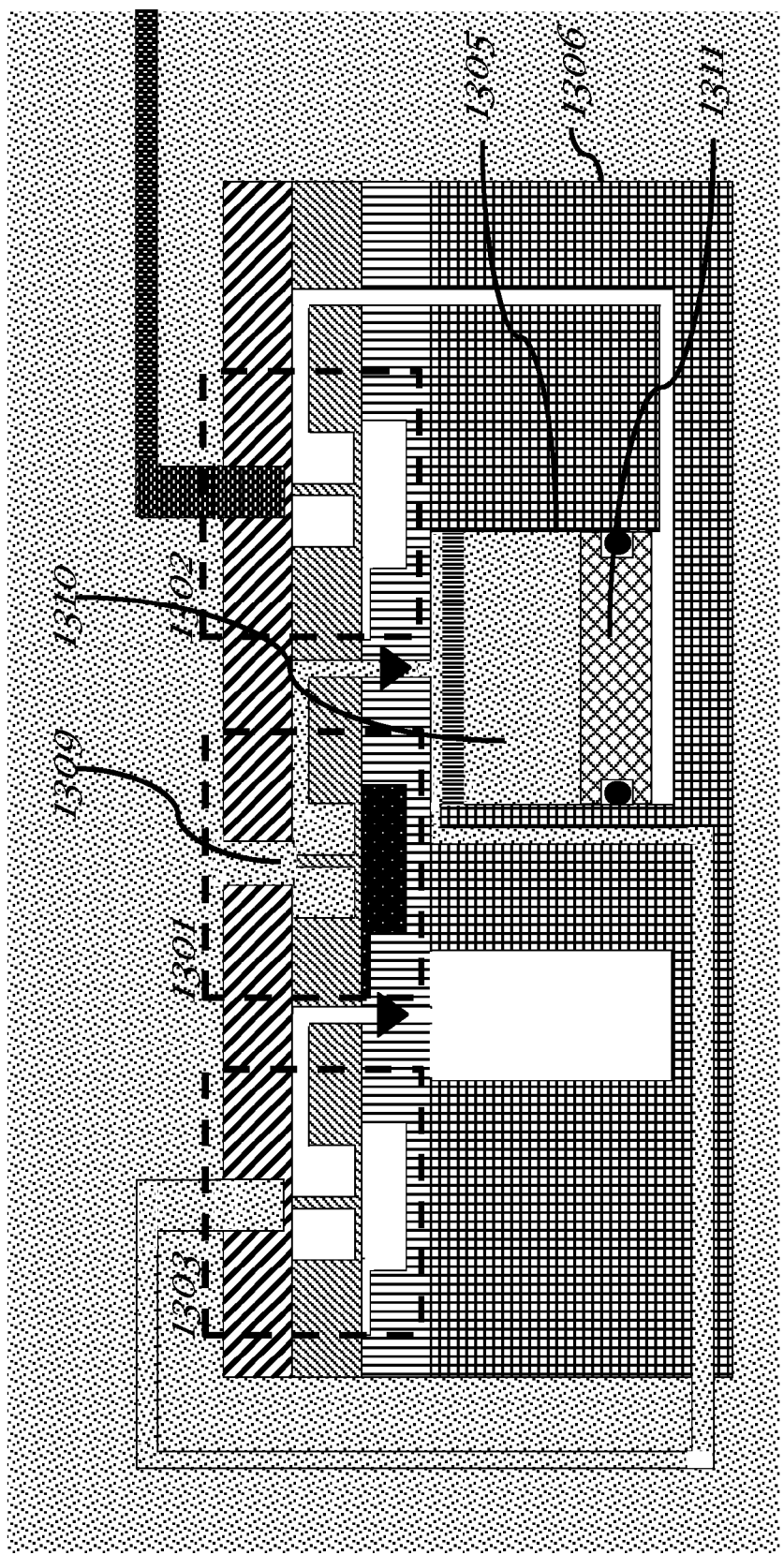
Fig. 13-B

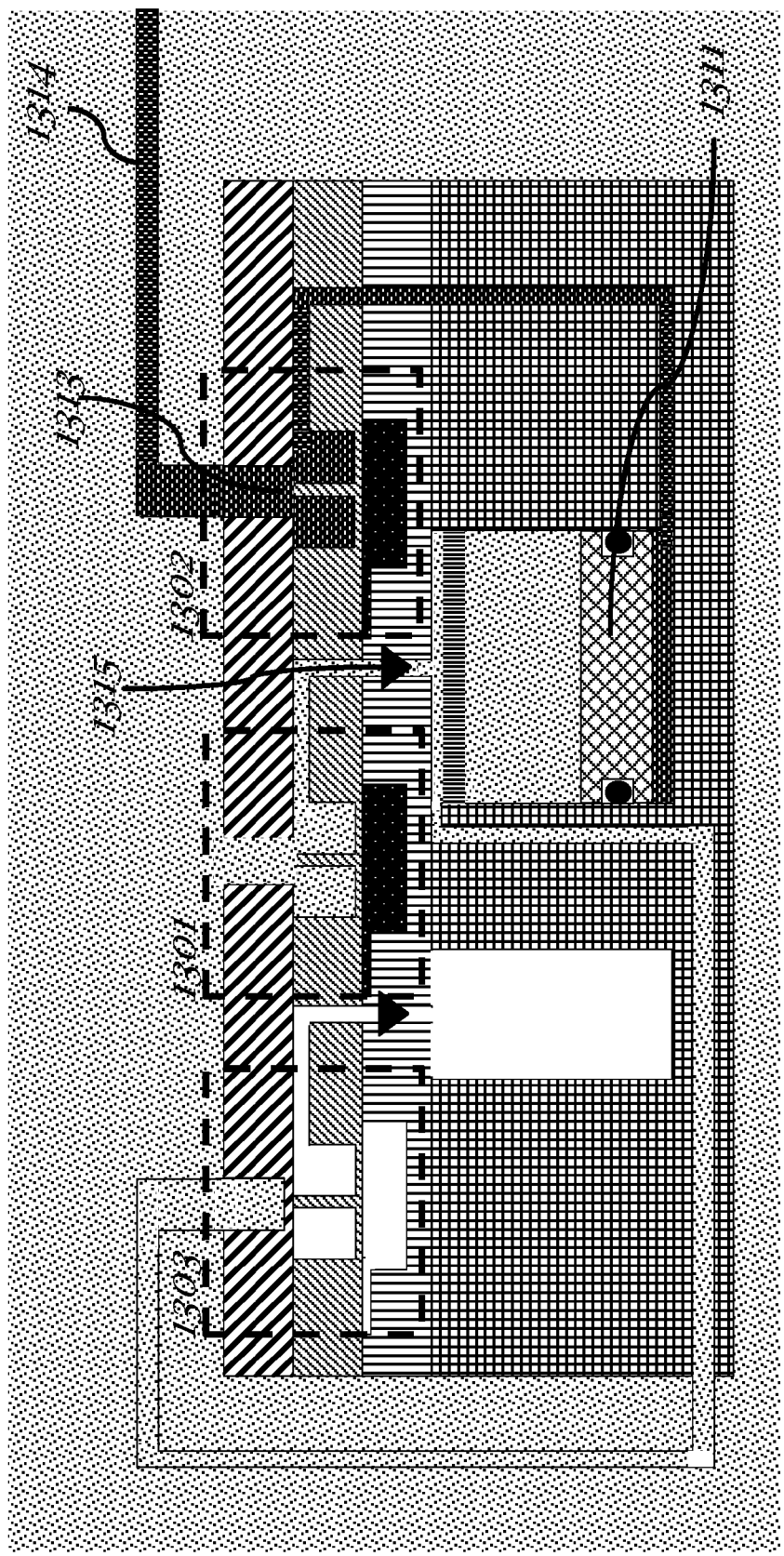
Fig. 13-C

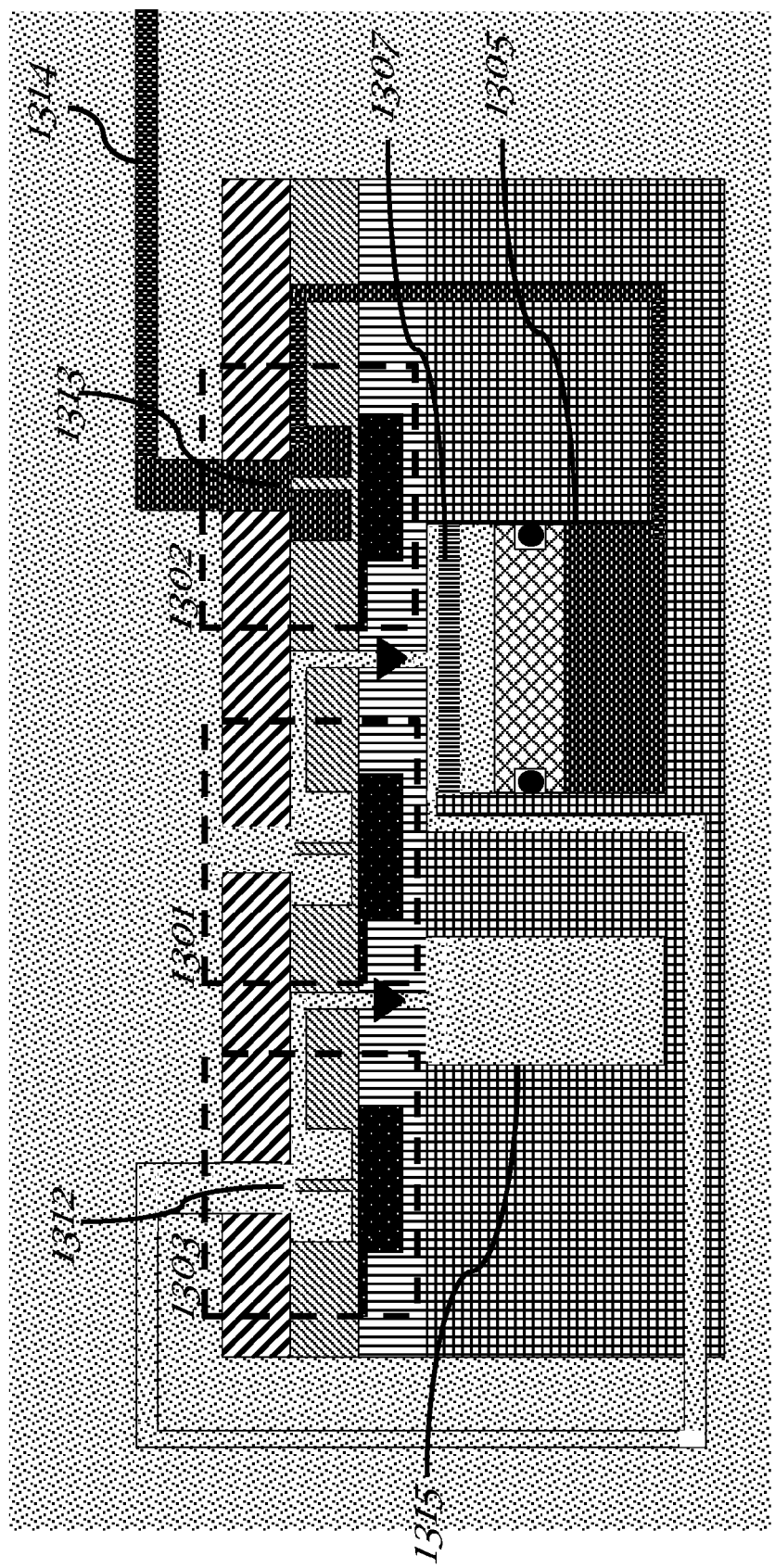
Fig. 13-D

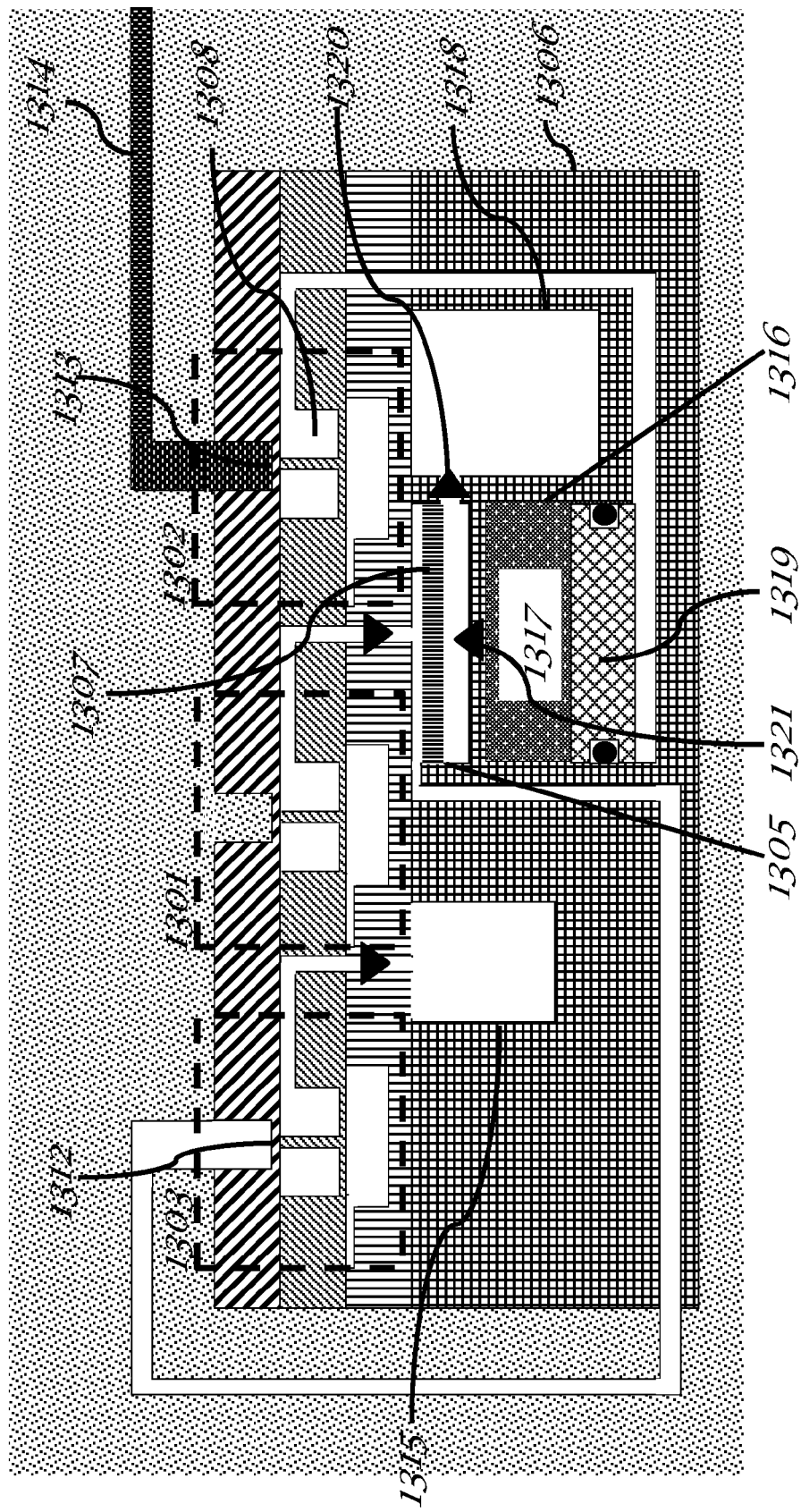
Fig. 13-E

PASSIVE MICRO-VESSEL AND SENSOR

CROSS-REFERENCE TO RELATED APPLICATIONS

This application is a continuation in part of U.S. application Ser. No. 13/025,467, filed Feb. 11, 2011, which in turn claims priority from U.S. provisional patent application Ser. No. 61/337,998 filed Feb. 12, 2010, entitled "Passive Microvessel and Sensor." Each of the above-described applications is hereby incorporated herein by reference, in its entirety.

TECHNICAL FIELD

The present invention generally relates to an electrically passive device capable of communicating its position by acoustic emission at specific time intervals, and/or of retrieving and/or sensing/and/or determining characteristics of fluid samples at, for example, specific time intervals, and/or of time-release of particles, chemical products, or pharmaceutical products. More particular embodiments of the present invention relate, for example, to an electrically passive vessel for acquiring samples or releasing various particle/products in a subsurface formation (such as a geological or marine formation) or a living body, with the optional capability of providing measurements on the sample, and/or communicating its position via acoustic emissions.

BACKGROUND ART

Obtaining and analyzing samples of fluid from subsurface reservoir formations is often conducted during oil and gas exploration. Such operations are hindered by the harsh subterranean environment specific to oilfields, including high temperature and pressure (HPHT), corrosive fluids, and severely constrained geometry. The difficulty in acquiring and performing measurements on fluidic samples in such an environment are further complicated by use of electronic sensors that typically require power, monitoring and/or telemetry.

Several oil-field related operations, such as fracturing a geological formation, would greatly benefit from the capability of producing a map of the subterranean fracture geometry, and of the fracture evolution in time. Such capability does not currently exist. A similar need exists for a technology which can be used in monitoring and performing fracture analysis of subterranean carbon dioxide sequestration reservoirs.

Measurements of fluid properties and composition far from an oil well are difficult to perform in the oilfield environment. The capability to inject very small sensing devices far into a geological formation by use of a Proppant or similar means of sensor transport, and to be able to determine their position and the precise moment when they perform a measurement or acquire a sample would greatly benefit the industry.

Measurements need to be performed in other types of situations, where the deployment of active sensing systems with on-board electronics and data transmission capabilities may either be impossible due to environmental issues (for example temperatures and pressures that are too high) or may prove to be too expensive to justify economically. Typical examples involve measurements within aquifers, potable water wells, or in a submarine environment. Such an environment may be a lake, or a sea or ocean. Still further environments include where or when there is a lack of power, such as in remote areas of the world.

The capability to perform viscosity measurements on fluid samples is extremely important in a variety of industries: chemical engineering, food industry, oilfield, to name a few. Usually this is accomplished using large laboratory instruments such as capillary viscometers and rheometers, or by using portable lighter weight instruments. In most cases, these instruments are operated using electrical power, and require sample manipulations that are difficult to automate. In some environments such instruments may be impractical due to their size (such as in difficult to reach areas, or within downhole oilfield tools), may be dangerous due to their electrical operation (inside explosive environments such as refinery facilities and tanks, near oil and gas wells), may be incompatible with the shocks or vibrations (within an oil well), or may be simply difficult to adapt. In this case new types of viscosity measurements need to be devised that avoid such inconveniences.

Samples often need to be acquired in explosive atmospheres (ATEX environments) such as inside refinery tanks (to determine the fluid quality and stratification), within refineries or gas plants or other facilities dealing with explosive environments. In such situations the sampling equipment should not pose a risk of generating an explosion, as would be the case if an electrical spark were created. All-mechanical systems that are ATEX-certified are currently used in the industry to perform this type of sampling.

Furthermore, samples may need to be acquired from fluids that are at high pressure, such as in a chemical factory, a refinery, inside an oil well, or at high depth within the ocean. When pressure is lowered, such samples may change (or degrade) by undergoing a thermodynamic phase transition leading to phase separation (i.e. gas may separate from oil, or asphaltenes may precipitate from heavy oil), in a possibly irreversible manner. Sample containers in this case may need to be filled slowly, at controlled inflow into the sample vial or chamber, in order to preserve the thermodynamic equilibrium and prevent, for example, a pressure shock that may lead to phase separation or other irreversible changes in the sample constituency. Such samples may also need to be maintained at high-pressure conditions subsequent to sample acquisition (for example during sample tool retrieval, or during transportation to a remote laboratory), to prevent sample degradation and maintain the sample characteristics unchanged.

Additionally, samples are often required in environments that pose objective risks and dangers, or that are physically remote, or where frequent sampling using manual devices may prove impractical: sites of nuclear disasters, military battlegrounds, biohazard or chemical hazard areas, terrorist attack sites, remote natural resources such as rivers and lakes, coastal waters and other offshore locations, deep water and sub-sea environments. In such cases, robotic equipment may need to be deployed, and the capability to take and analyze such samples may provide important information that cannot be acquired using the on-board in-line sensors present on such equipment. Such equipment may consist of autonomous or remotely-operated vehicles or robots; remotely-operated underwater vehicles; autonomous underwater vehicles such as buoyancy-driven gliders and wave gliders; airborne or ground drones; other type of robotic equipment.

Samples often need to be acquired and analyzed to detect trace levels of certain contaminants that may be too dilute to enable direct detection. Sample pre-concentration may be required in such cases, by methods such as filtration using mechanical filters, polymeric filters, fiber glass filters, affinity columns, solid phase extraction columns, gas chromatography pre-concentration tubes and columns, or other types of material showing particular affinity for the contaminant, and possibly included in porous or packed form. Particular care needs to be taken when acquiring such samples to prevent scavenging of the sample by, or its adsorption to, the materials of the sampling vial or chamber, or of the transport tubes. The filter material may need to be backflushed, often with a different solution, to remove filter cake buildup and to generate a pre-concentrated sample that may need to be stored into a separate vial or container for transport, storage, or for further manipulation and/or analysis. Alternatively, the filter itself may be retrieved and analyzed, after applying an optional extraction protocole, using laboratory equipment such as gas chromatography, high precision liquid chromatography (HPLC), mass spectroscopy, gamma ray spectroscopy, or other analytical chemistry, biochemical, biological, or nuclear equipment, and possibly after solvent or thermal desorption.

Often there is a need to perform a chemical or biochemical reaction on the acquired sample, by bringing it in contact with a known quantity of chemical or biochemical reagent that will lead to a property change as a consequence of the reaction. The chemical or biochemical reagent may be present as a liquid, solid, powder, gel, gas, emulsion or foam, and it may be attached to, or immobilized on, a solid substrate such as the walls of a vial, a strip of metal, tissue, plastic, paper (as is the case of colorimetric test strips). The reagent may be lyophilized. Often, the (bio)chemical reaction results in color change, which can be detected optically by spectrophotometric absorbance or by colorimetry. Other times direct fluorescence of the sample, or the presence of a fluorescent byproduct, can be detected by fluorescence measurements. Many other properties of the sample may be measured such as (without limitation) optical absorbance, chemiluminescence, color, turbidity, fluorescence intensity, index of refraction, conductivity, density, viscosity. In some cases the usage of a microplate with multiple wells may be necessary to prepare a sample and perform measurements on it.

Certain chemical or biochemical sample preparation protocols may require more complex sample manipulations, such as reaction with a first reagent, waiting for an incubation or reaction time, and then bringing the sample in contact with a second reagent. This sequence may need to be repeated several times.

For pollution monitoring, often samples are not acquired instantaneously but rather over longer periods of time. The rate of sample intake may be proportional to flow velocity in the body of water being sampled. This technique provides "integrated" water samples, which allow in some circumstances to determine the average pollution of the body of water over a period of time, rather than instantaneous pollution.

In certain applications, the moment when a sample needs to be acquired may not be known in advance, so that a pre-programmed sampling sequence may not be appropriate. In this case, individual control of the moment when each sample is performed may be required. For example, samples may need to be acquired in the aftermath of an unforeseen accident, or as directed by an external signal.

In some cases, there may be a need to acquire a larger number of samples than the capabilities of a single sampling device. In this case, multiple sampling devices may need to be used in a "daisy chain configuration", in such a way that once a device acquires its maximum number of samples, it automatically triggers the next device that will take over the sampling tasks. Using this approach, the total number of samples that can be acquired is not limited by the capabilities of an individual device.

Often there is a need for injecting, or liberating, small particles or small amounts of chemicals at predefined times into a remote environment, or into an environment which is difficult to access. Such small particles or chemicals may be used as tracers, may participate in chemical reactions, or may be used as pharmaceuticals. Exemplary environments where such particles, chemicals, or pharmaceuticals may be injected include without limitation oil and water reservoirs, pre-existing or induced fractures within such reservoirs or within other geological formations, oil, water and/or gas wells, water bodies such as lakes, rivers and oceans, or a human body.

Monitoring of hazardous waste disposal reservoirs and of adjacent aquifers for contamination mapping and leaching is also a very important domain, where the need for miniaturized and economical sensing solutions is prominent.

SUMMARY OF THE INVENTION

In accordance with an embodiment of the invention, a device includes at least one sampling mechanism. Each sampling mechanism includes a timing diaphragm, a timing cavity, a mechanical structure and an isolated cavity. Each sampling mechanism further includes a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching the timing cavity after a timing interval and filling it, the timing fluid applies pressure to the timing diaphragm which ruptures and/or collapses the mechanical structure, thus allowing the external fluid to enter the isolated cavity, which may then further lead to a sampling chamber.

In accordance with related embodiments of the invention, the mechanical structure may be made of an inorganic material, a non-polymeric material, silicon, glass, ceramic and combinations thereof. The mechanical structure may be insoluble in water, bodily fluids, oil, crude oil, oil field fluid, salt water, sea water and combinations thereof. The conduit may be, without limitation, initially at least partially filled the timing fluid, or in other embodiments, the timing fluid may be the external fluid that enters from the isolated cavity. The device may include a plurality of sampling mechanisms. At least one sampling mechanism may have a conduit having different dimensions than another sampling mechanism, such that the timing fluid of the different sampling mechanisms reach their associated cavities at different times. The sampling mechanism may include a check valve that allows flow of fluid into the sampling chamber but prevents flow of fluid out of the sampling chamber. The device may release a weight upon sample acquisition so as to maintain a constant mass and not modify its submerged weight and buoyancy.

In accordance with further related embodiments of the invention, a conduit, such as a microfluidic channel or capillary tube, may be implemented between the mechanical structure and the sampling chamber, or within the sample chamber itself, such that upon the collapse of rupture of the mechanical structure, the sample enters the sampling chamber at a low flow rate controlled by the conduit, and fills the sampling chamber over a controlled period of time.

In accordance with yet further related embodiments of the invention, the device may force the sample to come in contact, upon or prior to entering the sampling chamber, with a filter that may be one of the following (without limitation): a mechanical filter, a solid phase extraction column, a hydrocarbon filter, a gas chromatography preconcentrator, a filter to collect and concentrate radioactive material, a biological filter, an absorbent medium, a scavenging medium, a hydrophobic material, and hydrophilic material, or any combination thereof. The filters may, optionally, be later retrieved and analyzed, to provide time-series data concerning the contaminant of interest at the location of the device.

In accordance with further related embodiments of the invention, an acoustic signal may be emitted from the device upon the mechanical structure rupturing and/or collapsing. The isolated cavity and the mechanical structure may be shaped to emit a predetermined acoustic signal upon the mechanical structure collapsing. The device may include a plurality of sampling mechanisms, each sampling mechanism having an acoustic signature upon collapse of its associated mechanical structure, wherein the acoustic signatures of the sampling mechanisms vary. The device may include a plurality of sampling mechanisms, wherein at least one sampling mechanism has a conduit, such as a microfluidic channel or capillary tube, having different dimensions than another sampling mechanism, such that the timing fluid of the different sampling mechanisms reach their associated cavities at different times so as to produce multiple acoustic events that occur at different times. The sampling chamber may include a sensor element for performing a detection and/or a measurement on the fluid. The sensor element may include, for example, a material that interacts with the fluid and/or electrodes allowing an electrochemical measurement to be performed on the fluid sample. The device may be electrically passive. The isolated cavity may include a micro-particle, a nano-particle, a chemical product, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with still further related embodiments, a tool may incorporate the above-described device. The tool may have an interior flow-line through which a sample fluid is capable of circulating and in which the one or more devices are positioned, wherein said sample fluid when circulating in the interior flow-line contacts the devices. The tool may include a pad capable of being pushed into a formation wall to receive fluid, and a pump for pumping formation fluid into the interior flow-line. The tool may further include at least one microphone for receiving acoustic emissions from the one or more devices. Other microphones may be located at different positions on the ground in the area surrounding a well, or within wells drilled elsewhere in the formation. The tool may include a processor for performing a time-stamping of the received acoustic emissions and/or a determination of device positioning. The tool may include a retrieval mechanism for retrieving the devices from an underground formation. The retrieval mechanism may include one of a pumping device and a suction device.

In accordance with still further related embodiments, the above-described device may be injected from the surface into an underground formation by pumping it along with a carrier fluid or proppant through a well. Monitoring of the acoustic emissions from the device may be performed using microphones placed in the injection well, in a well drilled elsewhere in the area, or on the ground. The device may be deployed in a pipe, a well, an engine, a hydrocarbon reservoir, an aquifer, a body of water, an oil field tool, a waste disposal reservoir, a proppant formulation and/or a living body.

In accordance with another embodiment of the invention, a device for sampling a fluid includes at least one sampling mechanism, which may be electrically passive. Each sampling mechanism includes an isolated cavity, a mechanical structure and a microfluidic timing mechanism. Upon the microfluidic timing mechanism being subject to pressure, the mechanical structure collapses and/or ruptures after a time delay, allowing external fluid to enter the isolated cavity, which may then further lead to a sampling chamber.

In accordance with related embodiments of the invention, the microfluidic timing mechanism may include a conduit that may be a microfluidic channel or a capillary tube, and that may have a predefined geometry. Upon applying pressure to a timing fluid within the conduit, the timing fluid advances within the conduit at a speed, for example, that may be dictated by the predefined channel geometry and known timing fluid properties The microfluidic timing mechanism may include a timing cavity and a timing diaphragm, and wherein upon the timing fluid advancing and reaching/filling the timing cavity, the timing fluid applies pressure to expand the timing diaphragm, collapsing the mechanical structure and thus allowing the external fluid to enter the isolated cavity. The device may emit a predetermined acoustic signal upon collapse of the mechanical structure. The sample cavity may include a sensor element for performing a detection and/or a measurement on the fluid that enters the sample chamber. The isolated cavity may include a micro-particle, a nano-particle, a chemical product, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with further related embodiments of the invention, a system includes one or more of the above-described devices. The system further includes at least one microphone, geophone, accelerometer and/or other type of sensor for receiving acoustic emissions from the one or more devices. A processor may timestamp the received acoustic emissions and/or determine a position of the one or more devices based, at least in part, on the received acoustic emissions. The device may be deployed within a pipe, a well, an engine, a hydrocarbon reservoir, an aquifer, a body of water, an oil field tool, a waste disposal reservoir, a proppant formulation and/or a living body.

In accordance with another embodiment of the invention, a system for sampling a fluid includes at least one device, which may be electrically passive. Each device includes a mechanical structure, and a microfluidic timing mechanism that, upon the microfluidic timing mechanism being subjected to pressure, collapses the mechanical structure after a time delay. Upon collapse the mechanical structure emits an acoustic signature, and may allow fluid to enter a sample chamber. The system further includes a microphone for receiving the acoustic signature, and a processor operatively coupled to the microphone. The processor may, for example, extract the position of the device based, at least in part, on the received acoustic signature.

In accordance with another embodiment of the invention, a method includes deploying a device in a fluid. An acoustic cavity within the device is opened to the fluid at a time determined by an electrically passive timing mechanism. The device emits an acoustic signature when the cavity is opened.

In accordance with related embodiments of the invention, a sample may be acquired upon opening of the cavity. The acoustic signature may be detected using, at least in part, one or more microphones, geophone, accelerometer and/or other type of sensor. The detected acoustic signature may be time-stamped. The position of the device may be extracted from the detected acoustic signature using, without limitation, triangulation, compressional signal processing, and/or shear signal processing. The device may be deployed in a geological formation or a formation fracture. For example, the device may be pumped into the geological formation. Deploying the device may include using the device in a hydraulic fracturing operation. The device may be deployed in a fluid within a pipe, a fluid within a well, a fluid within an engine, a hydrocarbon reservoir, an aquifer, a body of water, a fluid within an oil field tool, a waste disposal reservoir, a proppant formulation and/or a living body.

In accordance with further related embodiments of the invention, the timing mechanism may include a timing diaphragm, a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching and filling the timing cavity after a timing interval, the timing fluid applies pressure to the timing diaphragm which opens the acoustic cavity within the device to the external fluid. The conduit may be, without limitation, initially at least partially filled with the timing fluid. In other embodiments, the timing fluid may be, without limitation, the external fluid that enters from the isolated cavity.

In accordance with still further embodiments of the invention, at least one of a micro-particle, a nano-particle, a chemical product, and a pharmaceutical product may be stored within the device into the external fluid upon collapse of the acoustic cavity. A sample of the external fluid may be stored within the device upon collapse of the acoustic cavity.

In accordance with another embodiment of the invention, a device includes an isolated cavity that is initially inaccessible to an exterior environment, and an electrically passive timing mechanism. A mechanical structure separates the isolated cavity from the exterior environment, such that at the end of a timing interval the timing mechanism acts on the mechanical structure in a way that ruptures and/or collapses it, thus bringing the isolated cavity in contact with the exterior environment.

In accordance with a related embodiment of the invention, the device timing mechanism may include a timing membrane, a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties Upon reaching and filling the timing cavity after a timing interval the timing fluid applies pressure to the timing diaphragm which collapses the mechanical structure, thus allowing external fluid to enter the isolated cavity. The conduit may be, without limitation, initially at least partially filled with the timing fluid. In other embodiments, the timing fluid may be, without limitation, the external fluid that enters from the isolated cavity.

In accordance with further related embodiments of the invention, the device may include an external device for applying pressure to the timing fluid. The mechanical structure may be an isolation membrane and/or diaphragm. The isolated cavity may include a sampling chamber, the sampling chamber including a check valve that allows flow of fluid into the sampling chamber but prevents flow of fluid out of the sampling chamber. An acoustic signal may be emitted from the device upon rupture of the mechanical structure. The isolated cavity and the mechanical structure may be shaped to emit a predetermined acoustic signal upon the mechanical structure collapsing. The isolated cavity may include a sensor element for performing a detection and/or a measurement on the fluid. The sensor element may include a material that interacts, such as chemically, with the fluid. The sensor element may include an electrode, allowing, for example, an electrochemical measurement to be performed on the fluid sample. The sensor element may be a Micro-Electro-Mechanical Systems (MEMS) device that may be microfabricated.

In accordance with further embodiments of the invention, the external device for applying pressure to the timing fluid may include a device such as an accumulator, that incorporates a piston or a membrane, to which a force is transmitted using any means known in the art, such as a cushion of compressed gas, or a mechanical spring, or contact with a reservoir of fluid that is itself pressurized. The said reservoir of fluid may be the external fluid itself. Alternatively, the external device for applying pressure to the timing fluid may include a flexible bag, itself placed within a pressurized reservoir, such as the pressure of the reservoir is transmitted to the timing fluid. Such a reservoir may be pressurized by any means known in the art, such as by using a compressed gas cushion, or a mechanical spring mechanism, or contact with a reservoir of fluid that is itself pressurized. The said reservoir of fluid may be the external fluid itself.

In accordance with further related embodiments of the invention, two systems, each including multiple sampling devices that are timed such as to acquire the corresponding samples at different times, may have the mechanical structure of the last sampling device of the first system connected to the timing fluid reservoir of the second system. At the same time, the sampling cavity of the last sampling device of the first system may be connected to the timing fluid channels of the second device. In this configuration, the collapse or rupture of the mechanical structure of the last sampling device of the first system triggers the start of the sampling using the second system, thus allowing the systems to be connected in a daisy-chain configuration.

In accordance with yet further embodiments of the invention, the isolated cavity may include a micro-particle, a nano-particle, a chemical product, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with additional related embodiments of the invention, the device may include a plurality of isolated cavities, a plurality of passive timing mechanisms, and a plurality of mechanical structures. At least one of the passive timing mechanisms may have a timing interval different from the other timing mechanisms, such that the mechanical structures associated with the at least one passive timing mechanism ruptures and/or collapses at a different time.

In accordance with still further related embodiments of the invention, a system may include a plurality of the above-described devices, wherein each device has an acoustic signature upon collapse of its associated mechanical structure, wherein the acoustic signatures of the devices vary. A system may include a plurality of the above-described devices, wherein at least one device has a conduit having different dimensions than another device in the system, such that the timing fluid of the different sampling mechanisms reach their associated cavities at different times so as to produce multiple acoustic events that occur at different times. A tool may incorporate one or more of the above-described devices, the tool having an interior flow-line through which a sample fluid is capable of circulating and in which the one or more devices are positioned, wherein said sample fluid when circulating in the interior flow-line contacts the devices. The tool may further include at least one microphone for receiving acoustic emissions from the one or more devices, and a processor for performing timestamping of the received acoustic emissions and/or determination of device positioning. A method using at least one of the above-described devices may include deploying the device within one of a pipe, a well, an engine, a hydrocarbon reservoir, an aquifer, a body of water, a waste disposal reservoir, an oil field tool, a proppant formulation and a living body.

In accordance with yet further related embodiments of the invention, a system may include a plurality of the above-described devices, wherein the system is incorporated into an underwater measurement system. The system may be attached or otherwise embedded in a cable. The cable may be further attached to a fixed buoy, or towed through a body of water by a ship or an underwater vehicle.

In accordance with another embodiment of the invention, a method includes deploying a device in an external fluid. A cavity is opened within the device to the external fluid, at a time determined by an electrically passive timing mechanism. Upon the cavity opening, a micro-particle, a nano-particle, a chemical product, and/or a pharmaceutical product is released from the cavity into the external fluid, and/or a sample of the external fluid may be stored within the device.

In accordance with related embodiments of the invention, the passive timing mechanism may include a timing diaphragm, a timing cavity; a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching the timing cavity after a timing interval, the timing fluid applies pressure to the timing diaphragm which opens the cavity within the device to the external fluid. The conduit may be, without limitation, initially at least partially filled with the timing fluid. In other embodiments, the timing fluid may be, without limitation, the external fluid that enters from the isolated cavity.

In accordance with further related embodiments of the invention, deploying the device may include pumping the device into a geological formation and/or a formation fracture. The device may be deployed in a pipe, a well, an engine, a hydrocarbon reservoir, an aquifer, a body of water, an oil field tool, a waste disposal reservoir, a proppant formulation and/or a living body.

In accordance with still further embodiments of the invention, the method may include emitting by the device an acoustic signature when the cavity is opened. The acoustic signature may be detected using, at least in part, one or more microphone. A position of the device may be extracted from the detected acoustic signature using triangulation, compressional signal processing, and/or shear signal processing.

In accordance with another embodiment of the invention, a device includes an electrically passive timing mechanism and a mechanical structure. At the end of a timing interval, the timing mechanism ruptures the mechanical structure so as to emit an acoustic signal.

In accordance with related embodiments of the invention, the device may include an isolated cavity, wherein the mechanical structure separates the isolated cavity from the exterior environment, and wherein rupturing the mechanical structure brings the isolated cavity in contact with the exterior environment. The mechanical structure may be an isolation membrane.

In accordance with further embodiments of the invention, the timing mechanism may include a timing diaphragm a timing cavity, and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon reaching and filling the timing cavity, the timing fluid applies pressure to the timing diaphragm which ruptures and/or collapses the mechanical structure, which thus may allow external fluid to enter the isolated cavity. The conduit may be, without limitation, initially at least partially filled with the timing fluid. In other embodiments, the timing fluid may be, without limitation, the external fluid that enters from the isolated cavity. The isolated cavity may include a sampling chamber, the sampling chamber including a check valve that allows flow of fluid into the sampling chamber but prevents flow of fluid out of the sampling chamber. The sampling chamber may include a sensor element for performing at least one of a detection and a measurement on the fluid. The sensor element may include a material that interacts with the fluid. The sensor element may include electrodes allowing an electrochemical measurement to be performed on the fluid sample.

In accordance with further related embodiments of the invention, the mechanical structure may be shaped to emit a predetermined acoustic signature upon rupturing. The device may be microfabricated.

In accordance with still further related embodiments of the invention, a system includes a plurality of the above-described devices, wherein each device has an acoustic signature upon rupture of its associated mechanical structure, wherein the acoustic signatures of the devices vary. The system may be incorporated into an underwater measurement system. The devices may be attached to a cable. The cable may be towed through a body of water by one of a ship and an underwater vehicle. The device(s) may be used during a hydraulic fracturing operation.

In accordance with various embodiments of the invention, the timing fluid in the above-described embodiments may either be a Newtonian fluid of known viscosity or a non-Newtonian fluid of known rheology. A complex non-Newtonian shear-thinning fluid may have a number of advantages, namely the fact that the non-Newtonian timing fluid will have a very high viscosity at low shear stress (i.e. at low applied pressure), but the viscosity will drop rapidly as the stress is increased. In various embodiments of the invention, a complex non-Newtonian fluid may be used as a timing fluid, resulting in a timing mechanism which only becomes active once the ambient pressure has reached a certain threshold value and providing additional versatility to the timing mechanism.

In accordance with another embodiment of the invention, a system includes one or more devices. Each device includes an isolated cavity that is initially inaccessible to an external fluid and an electrically passive timing mechanism. Each device further includes a mechanical structure that separates the isolated cavity from the exterior environment, such that at the end of a timing interval the timing mechanism acts on the mechanical structure to rupture and/or collapse the mechanical structure, thus bringing the isolated cavity in contact with the external fluid.

In accordance with related embodiments of the invention, the mechanical structure may be made of an inorganic material, a non-polymeric material, silicon, glass, or a ceramic, or combinations thereof. The mechanical structure may be insoluble in a liquid, such as water, bodily fluids, oil, crude oil, oil field fluid, salt water, or sea water, or combinations thereof.

In accordance with further related embodiments of the invention, the isolated cavity may be in fluidic communication with a sampling chamber. A one-way check valve may be included between the isolated cavity and the sampling chamber that allows fluid flow into the sampling chamber. The sampling chamber may include one or more chemical and/or biological reagents. The system may further include a filter for filtering fluid upon or prior to entering the sampling chamber. The filter may be a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, or a hydrophilic material, or a combination thereof.

In accordance with yet further related embodiments of the invention, the sampling chamber of a first device of the one or more devices may include a piston and/or a flexible membrane that separates the sampling chamber into a first portion and a second portion, with the first portion in fluidic communication with the isolated cavity. The second portion may be in fluidic communication with an auxiliary chamber via a conduit, wherein the second portion is initially filled with a secondary liquid, and wherein upon rupture and/or collapse of the mechanical structure, fluid from the external environment enters the sampling chamber and applies pressure to the piston, which moves at a rate based, at least in part, on the value of the pressure of the external fluid, the viscosity of the secondary liquid and/or the geometry of said conduit. The conduit may include a constriction or a capillary tube.

In accordance with still further related embodiments of the invention, the one or more devices may include a second device, wherein the mechanical structure of the second device separates the isolated cavity of the second device from a pressurized fluid. The isolated cavity of the second device is in fluidic communication with the second portion of the sampling chamber, such that at the end of a timing interval the timing mechanism of the second device acts on the mechanical structure of the second device to rupture and/or collapse the mechanical structure of the second device, thus bringing the isolated cavity of the second device and the second portion of the sample chamber in fluidic communication with the pressurized fluid. The timing mechanisms of the first and second device may be configured such that the mechanical structure of the second device ruptures and/or collapses after the mechanical structure of the first device ruptures and/or collapses.

In accordance with related embodiments of the invention, the one or more devices may include a third device having a mechanical structure in fluidic communication with the first portion of the sampling chamber, such that rupture and/or collapse of the mechanical structure of the third device allows fluid communication between the first portion of the sampling chamber and a second sampling chamber. The timing mechanism of the third device may be configured such that the mechanical structure of the third device ruptures and/or collapses after the mechanical structure of the second device ruptures and/or collapses. The sampling chamber and/or the second sampling chamber may include a reagent.

In accordance with further related embodiments, the first portion of the sampling chamber may include a filter for retaining certain components from fluid entering the sampling chamber, the filter positioned within the sampling chamber such that fluid flowing between the sampling chamber and the second sampling chamber transports the retained filtered components. The system may further include: a first reservoir between the piston and the first portion of the sampling chamber, the first reservoir filled with a fluid and/or a reagent solution in fluidic communication with the first portion, such that fluid can flow from the first reservoir to the first portion of the sampling chamber; and a second reservoir in fluidic communication with the first portion of sampling chamber, the second reservoir for receiving overflow from the first portion of the sampling chamber, wherein upon the collapse and/or rupture of the third devices mechanical structure, the fluid and/or reagent solution from the first reservoir flows through the filter and into the second sampling chamber.

In accordance with yet further related embodiments of the invention, the passive timing mechanism may include a timing diaphragm a timing cavity and a conduit that may be a microfluidic channel or a capillary tube, and that may have a predefined geometry. Upon applying pressure to a timing fluid within the conduit, the timing fluid advances within the microfluidic channel at a speed, for example, that may be dictated by the predefined channel geometry and known timing fluid properties. Upon the timing fluid reaching the timing cavity and filling it after a timing interval, the timing fluid applies pressure to the timing diaphragm which ruptures and/or collapses the mechanical structure thus allowing external fluid to enter the isolated cavity. The conduit may be, without limitation, initially at least partially filled with the timing fluid. In other embodiments, the timing fluid may be, without limitation, the external fluid that enters from the isolated cavity.

In accordance with still further related embodiments of the invention, the one or more devices may include a first and second device, wherein the isolated cavity of the first device is coupled to the timing cavity of the second device via a conduit. Upon rupture and/or collapse of the mechanical structure of the first device, external fluid enters the isolated cavity of the first device and further communicates with the timing cavity of the second device. The timing cavity of the second device fills and the external fluid pressure is applied to the timing diaphragm of the second device, causing the mechanical structure of the second device to collapse and/or rupture.

In accordance with yet further related embodiments of the invention, the system further includes a controller configured to determine viscosity of the external fluid based on, at least in part, a measurement associated with the time of rupture and/or collapse of the one or more devices. The measurement may be an acoustic measurement, an electronic measurement, or an optical measurement, or a combination thereof. The system may further include a third device, the isolated cavity of the second device in fluidic communication with the timing mechanism of the third device, wherein the timing mechanisms of the second and third devices differ.

In accordance with further related embodiments of the invention, the system may further include a manifold. The manifold is in fluidic communication with the isolated cavity of each device upon rupture and/or collapse of their associated mechanical structure. Additionally, a sampling conduit is in fluidic communication with the manifold and the external fluid. The sampling conduit may further be in communication with a reagent reservoir that holds a reagent. A mixer may be utilized for mixing the reagent and the fluid from the external environment. The sampling conduit may include a sensor for performing measurements on fluid within the sampling conduit.

In accordance with still further related embodiments of the invention, the system may include a first and a second group of the one or more devices, wherein the isolated chamber of one of the devices in the first group of devices is coupled to the timing mechanism of each of the devices in the second group, such that the mechanical structures of the second group rupture and/or collapse after the mechanical structure of the one of the devices. The external fluid of the at least one or more devices may differ.

In accordance with further related embodiments of the invention, the system may further include a triggering mechanism configured to turn on and/or off the timing mechanism of at least one of the devices upon an external command. The triggering mechanism includes a component selected from a check valve, a solenoid valve, a one-shot valve, a fluidic switch, a MEMS component, a detonator and any combination thereof.

In accordance with another embodiment of the invention, a method for determining viscosity of an external fluid is provided. The method includes deploying a system in an external fluid, the system including a plurality of devices. An isolated cavity of a first device is opened at a time determined by an electrically passive timing mechanism of the first device, such that the external fluid enters the isolated cavity of the first device. The isolated cavity of the first device is in fluidic communication with a timing mechanism of the second device. An isolated cavity of a second device is opened at a time determined by the timing mechanism of the second device. Viscosity of the external fluid is determined based on, at least in part, a measurement associated with the opening of the isolated cavities of the first and second devices.

In accordance with related embodiments of the invention, the passive timing mechanism of each device may include a timing diaphragm, a timing cavity; and a conduit in fluidic communication with the timing cavity. Upon applying pressure to a timing fluid within the conduit, said timing fluid advances within the conduit and upon reaching the timing cavity and filling it after a timing interval, the timing fluid applies pressure to the timing diaphragm which ruptures and/or collapses the mechanical structure thus allowing external fluid to enter the isolated cavity.

In accordance with further related embodiments of the invention, determining viscosity may include performing a measurement, such as an acoustic measurement, an electronic measurement, an optical measurement, or combinations thereof.

In still further related embodiments of the invention, the isolated cavity of the second device is in fluidic communication with a timing mechanism of a third device. The method further includes opening an isolated cavity of the third device, at a time determined by the timing mechanism of the third device, wherein the timing mechanisms of the second and third devices differ. Determining viscosity of the external fluid may be based on, at least in part, a measurement associated with the opening of the isolated cavities of the first, second and third devices.

In accordance with another embodiment of the invention, a method includes deploying a system in an external fluid, the system including one or more devices. An isolated cavity of a first device of the one or more devices is opened, at a time determined by an electrically passive timing mechanism of the first device, such that the external fluid enters the isolated cavity of the first device, the isolated cavity of the first device in fluidic communication with a sampling chamber.

In accordance with related embodiments of the invention, the sampling chamber may include one or more chemical and/or biological reagents. The method may include filtering the fluid upon or prior to entering the sampling chamber. The filter may be a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, a hydrophilic material, or combination thereof. The method may include preventing backflow of the fluid from the sampling chamber to the isolated cavity.

In accordance with yet further related embodiment of the invention, the sampling chamber of the first device may include a piston and/or a flexible membrane that separates the sampling chamber into a first portion and a second portion, the first portion in fluidic communication with the isolated cavity. The second portion may be in fluidic communication with an auxiliary chamber via a conduit, wherein the second portion is initially filled with a secondary liquid, and wherein upon opening the isolated cavity of the first device, the external fluid enters the first portion of the sampling chamber and applies pressure to the piston, which moves at a rate based, at least in part, on the value of the pressure of the external fluid, the viscosity of the secondary liquid and/or the geometry of said conduit.

In accordance with still further related embodiments of the invention, the one or more devices may include a second device, an isolated cavity of the second device in fluidic communication with the second portion of the sampling chamber. The method may further include opening the isolated cavity of a second device, at a time determined by a timing mechanism of the second device, bringing the isolated cavity of the second device and the second portion of the sample chamber in fluidic communication with a pressurized fluid. The timing mechanisms of the first and second device are configured such that the mechanical structure of the second device ruptures and/or collapses after the mechanical structure of the first device ruptures and/or collapses.

In accordance with further embodiments of the invention, the one or more devices may include a third device having a mechanical structure in fluidic communication with the first portion of the sampling chamber. The method further includes rupturing and/or collapsing the mechanical structure of the third device, allowing fluid communication between the first portion of the sampling chamber and a second sampling chamber. A timing mechanism of the third device is configured such that the mechanical structure of the third device ruptures and/or collapses after the isolated cavity of the second device opens. The sampling chamber and/or the second sampling chamber may include a reagent.

In accordance with still further related embodiments of the invention, the method may include filtering components from fluid entering the sampling chamber, the filtering positioned within the sampling chamber such that fluid flowing between the sampling chamber and the second sampling chamber includes the filtered components. There may be a first reservoir between the piston and the first portion of the sampling chamber, the first reservoir filled with a fluid and/or a reagent solution in fluidic communication with the first portion, such that fluid can flow from the first reservoir to the first portion of the sampling chamber. There may be a second reservoir in fluidic communication with the first portion of sampling chamber, the second reservoir for receiving overflow from the first portion of the sampling chamber, wherein upon opening the third devices mechanical structure, the fluid and/or reagent solution from the first reservoir flows through the filter and into the second sampling chamber.

In accordance with another embodiment of the invention, an electrically passive sampling device such as in the described-above embodiments, may be used to sample fluid in highly flammable or explosive environment, such as refinery equipment, pipes and tanks, fuel tanks, gas tanks, oilfield separation reservoirs, oilfield production and exploration rigs, oilfield wellhead equipment. The intrinsic electrically-passive nature of the device assures that no electrical spark risk is present, by design. Such a sampling device may furthermore be used to acquire individual samples at different times, or at different depths. This would allow, for example, the acquisition of samples at different depths within a refinery tank to understand the details of the composition variations by depth, or of the stratification that may take place in such tanks.

In accordance with another embodiment of the invention, an electrically passive sampling device such as in the described-above embodiments, may be placed near a nuclear facility, in an atmospheric and/or aquatic environment, the start of the sampling program being triggered upon the occurrence of an external event such as, without limitation, an accident alert, a power outage, a military attack, a terrorist attack and/or a natural disaster.

In accordance with another embodiment of the invention, an electrically passive device/system such as in the described-above embodiments, is deployed in an urban or suburban location, the start of the sampling program being triggered upon the occurrence of an external event such as, without limitation, an accident alert, a chemical accident, a nuclear accident, a military attack, a terrorist attack and/or a natural disaster.

In accordance with another embodiment of the invention, an electrically passive device/system such as in the described-above embodiments, is mounted on a water supply line or pipe. Sampling may be triggered by an external event such as, without limitation, a user signal, a signal from an in-line measurement system, an external event such as an accident alert, a military attack, a terrorist attack and/or a natural disaster.

In accordance with another embodiment of the invention, an electrically passive device/system such as in the described-above embodiments, is mounted on a ground-based or aerial vehicle, robot or drone. Sampling may be triggered by an external event such as, without limitation, a user signal, a signal from an in-line measurement system, an external event such as an accident alert, a military attack, a terrorist attack and/or a natural disaster.

In accordance with another embodiment of the invention, an electrically passive device/system such as in the described-above embodiments, is mounted on a submerged device such as, without limitation, a mechanical structure, a rig, a cable, a submarine, a remotely operated underwater vehicle, an autonomous underwater vehicle, a glider, a ship or a buoy. Sampling may be triggered by an external event such as, without limitation, a user signal, a signal from an in-line measurement system, a signal from the submerged device, a fluorescence signal, an external event such as an accident alert, a military attack, a terrorist attack and/or a natural disaster.

In accordance with another embodiment of the invention, a multitude of devices/systems such as in the above-described embodiments may be deployed at different locations surrounding a structure to be monitored, such that the data collected from analyzing the different samples, either in-situ or after retrieval, is used to generate a map of the evolution of the component of interest in multiple dimensions (up to three spatial coordinates and time). Example could be the monitoring of the pollution generated by an offshore oil well, from a tanker or pipe accident, from a chemical plant, from a nuclear power plant, from car traffic, contamination from a military attack or from a terrorist attack and/or a natural disaster.

BRIEF DESCRIPTION OF THE DRAWINGS

The foregoing features of the invention will be more readily understood by reference to the following detailed description, taken with reference to the accompanying drawings.

FIGS. 2(*a*-*d*) show the device of FIG. 1 in more detail, in accordance with an embodiment of the invention. FIG. 2(*a*) shows the device prior to activation. FIG. 2(*b*) shows the device with the isolation membrane collapsed. FIG. 2(*c*) shows the device with the sample chamber filled with sample fluid. FIG. 2(*d*) shows the device ready to be interrogated after surface retrieval.

FIG. 3(*b*) shows multiple microphones placed at different positions in the formation, for recording the arrival time of the wavefronts caused by ruptured isolation membranes, in accordance with an embodiment of the invention.

FIG. 4 shows a passive timing device that includes a pharmaceutical product for release within a human body, in accordance with an embodiment of the invention.

FIG. 5 shows a passive timing device that includes a filter for containing the broken diaphragm particles, in accordance with an embodiment of the invention.

FIG. 8A shows a viscosity measurement system that may be fully passive, in accordance with an embodiment of the invention. FIG. 8B shows another viscosity-measurement system, in accordance with an embodiment of the invention.

FIG. 9A shows a sampling and measurement system that includes a manifold, in accordance with an embodiment of the invention. FIG. 9B shows an external sampling conduit connected via a T-junction to a reagent reservoir, in accordance with an embodiment of the invention.

FIG. 10A shows a device that may be used to acquire a sample from a contaminated external fluid, in accordance with an embodiment of the invention. FIG. 10B shows the device of FIG. 10A after sampling, in accordance with an embodiment of the invention.

FIGS. 11A-C shows a system capable of acquiring a sample from an external fluid, and maintaining it at a desired pressure for extended periods of time, in accordance with an embodiment of the invention. FIG. 11A shows the system prior to acquiring a sample. FIG. 11B shows the system after acquiring the sample. FIG. 11C shows the system after sample pressurization.

FIG. 12A shows a device for performing a sampling operation from a high-pressure external fluid without shocking the fluid, in accordance with an embodiment of the invention. FIG. 12B shows the device of FIG. 12A that further allows the sample to be maintained at a high pressure after sampling, in accordance with an embodiment of the invention.

FIGS. 13A-D show, in chronological order, operations performed by a system that, in addition to sampling at a time controlled by a passive timing mechanism, integrates a mechanism allowing the subsequent transfer of the sample from an initial sampling chamber to another sampling chamber after a given amount of time, in accordance with an embodiment of the invention. FIG. 13A shows the system prior to acquiring a sample. FIG. 13B shows the system after collapse of a first device's mechanical structure. FIG. 13C shows the system after the later collapse of a second device's mechanical structure. FIG. 13D shows the system after the later collapse of a third device's mechanical structure. FIG. 13E shows the system of FIGS. 13A-D modified such that the sampling chamber 1305 including a first reservoir and a second reservoir.

DETAILED DESCRIPTION OF SPECIFIC EMBODIMENTS

In illustrative embodiments, an electrically passive device and method for in-situ acoustic emission, and/or releasing, sampling and/or measuring of a fluid or various material(s) is provided. The device may provide a robust timing mechanism to release, sample and/or perform measurements on a pre-defined schedule, and, in various embodiments, emits an acoustic signal sequence(s) that may be used for triangulation of the device position within, for example, a hydrocarbon reservoir or a living body. Details are discussed below.

Figure 1:
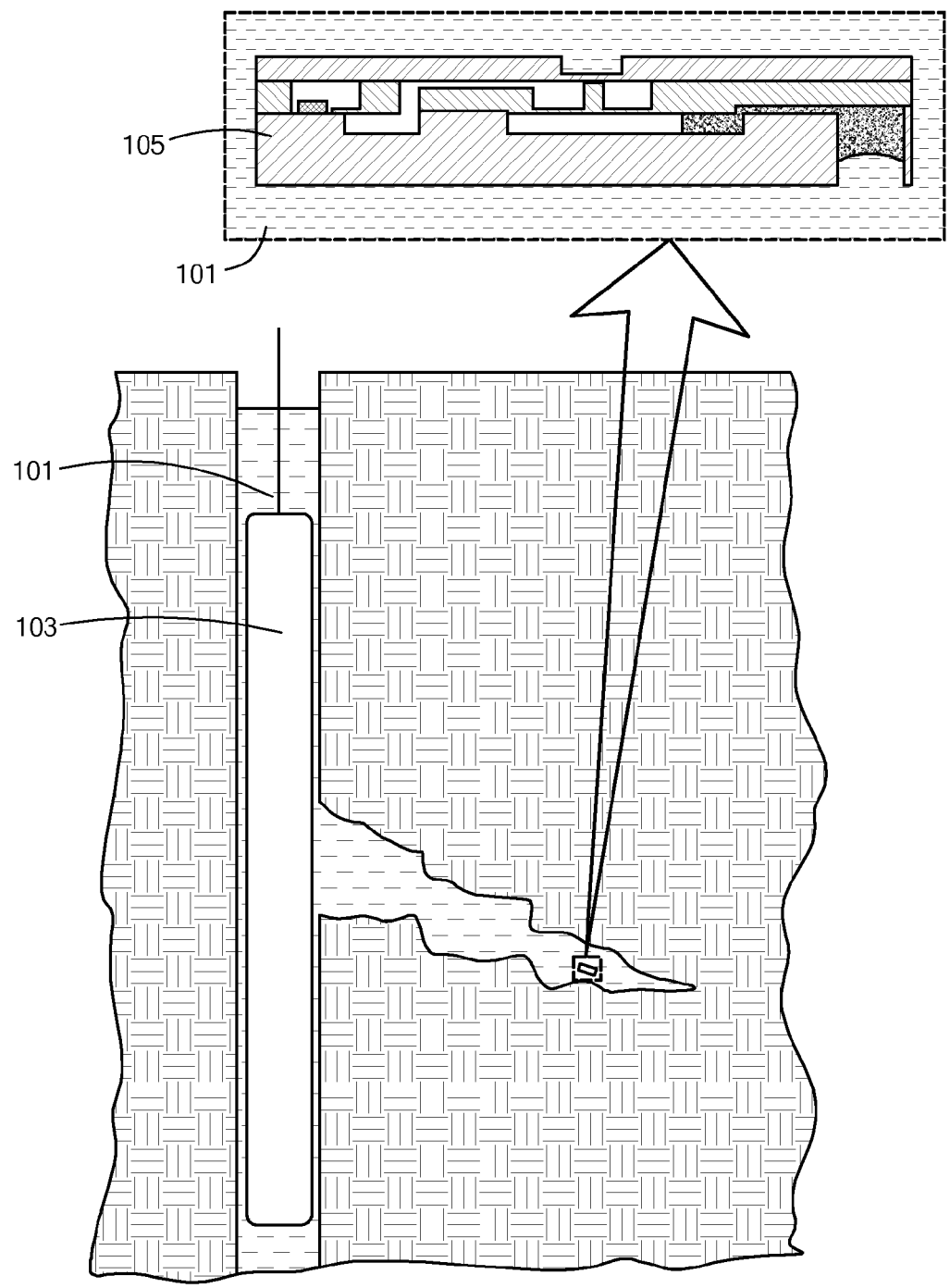
FIG. 1 shows deployment of a device for use in sampling hydrocarbons during fracturing or fluid injection operations, in accordance with an embodiment of the invention.

FIG. 1 shows deployment of a device 105 for use in sampling hydrocarbons during fracturing or fluid injection operations, in accordance with an embodiment of the invention. It should be noted that discussion of the specific device 105 shown, for use in sampling hydrocarbons, is for illustrative purposes only. Other device configurations and applications are within the scope of the present invention. For example, the device 105 may be deployed in a wide range of environments including, without limitation, within a pipe, a well, an engine, a hydrocarbon reservoir, an aquifer, a body of water, an oil field tool, a waste disposal reservoir, a proppant formulation and a living body to release, sample or measure various fluids (including a gas) or other material(s).

The device 105 may be deployed, without limitation, in downhole fluid 101 within a fracture in an underground formation. The device may be, for example, pumped or otherwise injected, into the rock matrix. The device 105 may work in combination with conventional oilfield measurement tools 103 or autonomous battery-operated sensors, that may be placed in the well in hydraulic communication with the fracture where the device 105 is injected. The device 105 may be used at very high pressures or temperatures, thus providing a pathway to performing measurements within wells which are currently inaccessible to existing sensor technology due to, without limitation, severely constrained geometry, corrosive fluids, elevated pressure and/or temperature. Examples of adverse well environments include recently developed deep-sea well reservoirs in the Gulf of Mexico. The device 105 may be used in areas with no available power. The device 105 may be used in explosive environments or atmospheres, where electric equipment poses a risk of explosion. The device 105 may be used for water and/or air quality monitoring in and around cities, chemical plants, nuclear sites, offshore platforms and other oilfield structures, military missions and battlegrounds. The device 105 may be used in robots such as marine remotely-operated underwater vehicles, autonomous underwater vehicles, airborne or ground drones and vehicles, and other types of robotic equipment. The device 105 may be used where and/or when there is no power available, such as in certain remote area.

The device may be of any size, dependent for example, on the application. In various embodiments, the device may be fabricated, at least in part, using micromachining or micro system technology, using, for example, silicon, glass and/or ceramics. In various embodiments, certain portions of the device may not be included in the micromachined process, such as the sampling chamber (described in more detail below), which may be, for example, a separate vial or other container.

FIGS. 2(a-d) show the device in more detail, in accordance with various embodiments of the invention. FIG. 2(a) shows the device 200 prior to activation. The device 200 includes at least one sampling mechanism for obtaining a sample of the external oil-well fluid 210.

In illustrative embodiments, the sampling mechanism includes a microfluidic timing mechanism for obtaining the fluidic sample. More particularly, the microfluidic timing mechanism may include a conduit that may be a microfluidic channel 202 or a capillary tube. The conduit may be partially filled with a timing fluid 201 (in other embodiments, the timing fluid may be without limitation, the external fluid that enters from the isolated cavity 206, described in more detail below). Capillary trapped timing fluid 201 may initially be held in place within the microfluidic channel by, without limitation, surface tension. The microfluidic channel 202 leads to a timing cavity 204 that may be of known volume. The timing cavity 204 may initially be, without limitation, empty.

Upon applying pressure to the timing fluid 201, the timing fluid 201 advances within the microfluidic channel 202 into the timing cavity 204 such that it causes a mechanical structure 205 to rupture (and/or collapse) after a time delay. The mechanical structure 205 may be insoluble in the environment or fluid in contact with the device. The mechanical structure 205 may be insoluble in water, bodily fluids, oil, oil field fluid, crude oil, salt water, or sea water, or combinations thereof. The mechanical structure 205 may be made of an inorganic material, a non-polymeric material, silicon, glass, or a ceramic, or combinations thereof. As used in this description and the accompanying claims, the term "inorganic" shall have the meaning indicated, unless the context otherwise requires: a material composed of atoms or molecules not containing carbon with, the exception of certain forms of carbon such as graphene, diamond, nanotubes and buckyballs, which shall be considered inorganic. Examples of inorganic materials include, without limitation, all metals, all types of glasses, silicon compounds such as oxides and nitrides, ceramic materials, silicon (in all crystalline forms), quartz, diamond, sapphire, ruby, as well as all materials of geologic origin.

In accordance with various embodiments, the timing fluid may be routed, prior to entering the timing channel, through a trigger device that can enable or disable the passage of timing fluid as desired. The trigger device may be one of a check valve, an electrically-controlled solenoid valve, a fluidic switch, or any other type of active valve known in the art. Examples of different types of valves used in microfluidic devices are provided in "Components for integrated poly (dimethylsiloxane) microfluidic systems" Electrophoresis 2002, 23, 3461-3473; "Micro Total Analysis Systems: Latest Achievements" Anal. Chem. 2008, 80, 4403-4419, incorporated herein by reference in its entirety. The trigger device may also include a one-shot valve that initially blocks the passage of timing fluid and upon receipt of an external signal permanently opens the passage of timing fluid without requiring further power.

Prior to rupturing, the mechanical structure 205 isolates an isolated cavity 206, which may include a sample chamber 209, from the external environment, which may include an external fluid (which may be a gas). The mechanical structure 205 may be, without limitation, an isolation diaphragm or isolation membrane that provides a barrier from the external environment. An example of a delayed actuator with a visco-elastic timer is described in U.S. Pat. No. 4,791,251 (Carter et al.), which is hereby incorporated by reference, in its entirety.

Illustratively, the timing fluid 201 entering the timing cavity 204 may cause a timing diaphragm 203 to deflect. A protrusion or other shaped structure on the timing diaphragm 203 may then rupture the mechanical structure 205. Various other membrane rupture mechanisms known in the art of microfluidic systems, such as in systems used to provide drug encapsulation and delivery, may be utilized (see, for example, M. Staples et al.: Pharm. Res., 23, 847 (2006); J. T. Santini et al.: Angew. Chem. Int. Ed. 39, 2396 (2000); J. H. Prescott et al.: Nat. Biotech. 24, 437 (2006), U.S. Pat. No. 7,455,667 (B2), each of which is incorporated herein by reference in its entirety).

FIG. 2(b) shows the device 200 with the mechanical structure 205 collapsed after applying pressure to the timing fluid 201 (and after the time delay). The collapse of the mechanical structure 205 allows external downhole fluid to enter a sample chamber 209 via an isolated cavity/communication channel 206. The sample chamber 209 may be pre-vacuumed or hold a gas prior to deployment of the device 200. A particle filter may be placed within the isolated cavity/communication channel 206 to filter any contaminants. Note that prior to collapse of the mechanical structure 205, the isolated cavity/communication channel 206 is typically inaccessible to the exterior environment. In other embodiments, the mechanical structure 205 may allow partial/filtered access to the isolated cavity/communication channel 206 prior to its collapse.

FIG. 2(c) shows the device 200 with the sample chamber 209 filled with sample fluid. An integrated one-way valve 207 (i.e., a check valve), may assure sample isolation from the external environment. An example of a micro-fabricated one-way valve is described in the following documents: S. Beeby, G. Ensel, M. Kraft: *MEMS Mechanical Sensors*, Artech House, Boston Mass. (2004); and K. W. Oh et al.: J. Micromech. Microeng., 16, R13-R39 (2006), each of which is incorporated herein by reference in its entirety.

The timing mechanism, the sampling mechanism, and/or in various embodiments, the entire device, may be electrically passive such that it does not include any powered electronic components (e.g., an electronic power source, transmitter, amplifier etc. . . . ). In various embodiments, the timing mechanism, the sampling mechanism, and/or the entire device may be void of any active or passive electronic components.

The passive microfluidic timing mechanism may be based, at least in part, on the fact that the flow rate f of a Newtonian fluid through a capillary of roughly circular cross-section is proportional to the difference in pressure $\Delta P$ between the ends of the capillary multiplied by the fourth power of the hydraulic radius R, and is inversely proportional to the viscosity of the fluid $\eta$ multiplied by the length of the capillary l: $f = \pi \cdot \Delta P \cdot R^4 / (8 \cdot \eta \cdot l)$. In other embodiments, if the capillary is chosen to have a rectangular cross-section with width w and height $h<w$, the flowrate f can be calculated with the approximate formula: $f = (1 - 0.63 h/w) \cdot \Delta P \cdot w \cdot h^3 / (12 \cdot \eta \cdot l)$. Such formulae may be found in the literature, for example in the following documents: Stone, H., Stroock, A., and Ajdari, A., "Engineering Flows in Small Devices," Annual Review of Fluid Mechanics, Vol. 36, 2004, p. 381 and D. E. Angelescu: "Highly Integrated Microfluidics Design", Artech House, Norwood Mass. USA (2011), each of which is incorporated herein by reference in its entirety.

If an empty cavity of known volume (i.e., the timing cavity 204) is separated from a high-pressure fluid by a capillary of appropriate geometry, the time required to fill the timing cavity 204 can be accurately determined from knowledge of device geometry, fluid viscosity and pressure differential. Assuming the timing fluid 201 has known characteristics, and that the pressure/temperature history is recorded, the filling time of the timing cavity 204 can be fully determined by geometrical device parameters such as timing cavity 204 volume, microfluidic channel 202 capillary diameter and length; the fourth power dependence on diameter allows control of the fill-up time over several decades, resulting in a very versatile timing mechanism. A fully characterized timing fluid 201 may be used that advantageously may be immiscible with both hydrocarbons and water. Examples of such timing fluids include, without limitation, various silicone oils and fluorinated solvents.

Alternatively, a non-Newtonian fluid with known rheological properties can be used as a timing fluid. In one embodiment, one may use a shear-thinning fluid as a timing fluid, which will result in a flowrate which is very low at low pressures, but increases significantly once the ambient pressure (and hence the shear stress in the microchannel) reaches a certain threshold value. In another embodiment, the timing fluid may be a visco-elastic fluid which behaves as an elastic body at low shear stresses, thus completely blocking flow at low pressures. As the pressure reaches a threshold value (corresponding to the yield stress of the timing fluid), the timing fluid will start flowing. This embodiment allows the passive timing devices described above to be inactive below a certain threshold pressure, thus allowing prolonged storage at a pressure situated below the threshold pressure.

FIG. 2(d) shows the device 200 ready to be interrogated after surface retrieval. The sample fluid stored in the sample chamber 209 remains isolated from the environment by the one-way valve 207, so that various physical and chemical property measurements can be obtained. A sensor 208 may be positioned within, or otherwise operationally coupled to, the sample chamber 209 and/or isolated cavity 206, so as to provide various indications or measurements associated with the sample fluid. In various embodiments, a micro-electro-mechanical sensor (MEMS) design may provide hermetic encapsulation of sensor components within, for example, the sample chamber 209. The sensor 208 may include a material that chemically reacts with the fluid, and/or an electrode allowing an electrochemical measurement to be performed on the fluid sample.

The above-described timing mechanism in conjunction with passive actuators may thus be used to deploy self-triggering sample acquisition devices/vessels. For deployment within a rock matrix, such devices may be density-matched to an injection fluid by incorporating vacuum cavities of appropriate dimensions, which will facilitate passive deployment by injection as well as device retrieval.

Acoustic Emission and Triangulation

Figure 3A:
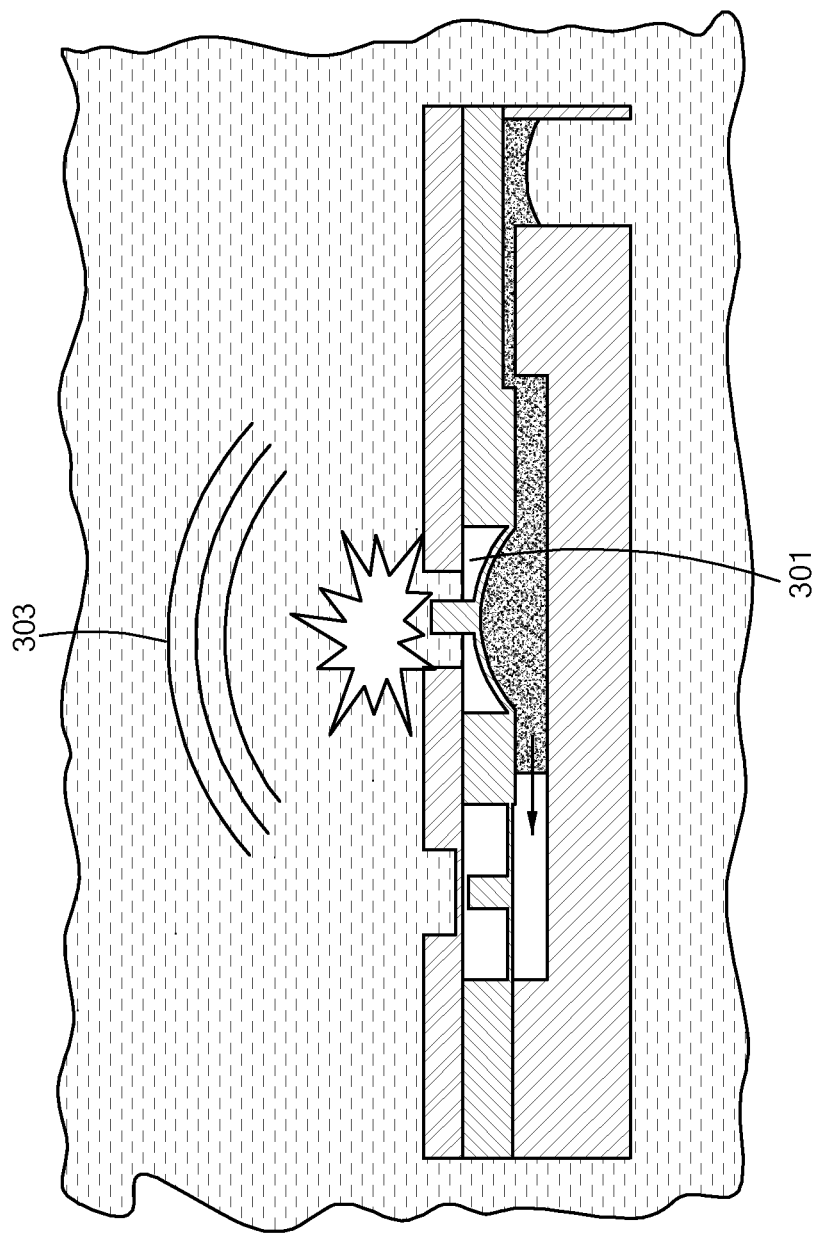
FIG. 3(*a*) shows a burst of acoustic energy resulting from the rupturing of an isolation membrane, in accordance with an embodiment of the invention.

The above-described device for sample acquisition may be used to generate acoustic signals. For example, in various embodiments the timing mechanism may trigger the piercing of multiple mechanical structures/isolation diaphragms, possibly in sequence. For example, if the cavity behind each isolation diaphragm has volume V (initially under vacuum), upon piercing, these cavities will suddenly collapse and/or rupture, and fill with reservoir fluid at the ambient hydrostatic pressure. The filling of the empty cavity 301 may be very sudden, and will emit a very short burst of acoustic energy 303, as shown in FIG. 3(a), in accordance with an embodiment of the invention. Laboratory studies of collapsing bubbles have been performed by others (for example, A. VOGEL, W. LAUTERBORN, R. TIMM: "Optical and acoustic investigations of the dynamics of laser-produced cavitation bubbles near a solid boundary", J. Fluid Mech., Vol. 206, pp. 299-338 (1989), which is incorporated herein by reference in its entirety), proving that the majority of the bubble energy is emitted into the acoustic transients. The total amount of energy that may be released by sudden filling of a cavity may be roughly estimated as $E=pV$, where p is the reservoir pressure. For an exemplary volume of 1 $mm^3$ and an ambient pressure of 1000 Bar (app. 14500 psi), this corresponds, without limitation, to an emission energy of 100 mJ in a time interval of approximately a fraction of a thousandth of a second to a few thousandths of a second. This corresponds to an acoustic power of over 10-1000 W during each collapse event. Such acoustic emission can then be detected and recorded using remote microphones, hydrophones, geophones, accelerometers or other types of sensors or recorders.

The timing mechanism may trigger several acoustic events in sequence, with the time delay between consecutive collapses defined by the geometry of the associated microfluidic channel and timing cavity. Each device and/or sampling mechanism may be built with a different timing sequence, or with different geometrical parameters, to provide a unique acoustic signature. Such devices may also be realized without a sampling cavity, with the sole purpose of emitting a sound at a time determined by the microfluidic timing mechanism.

Figure 3B:
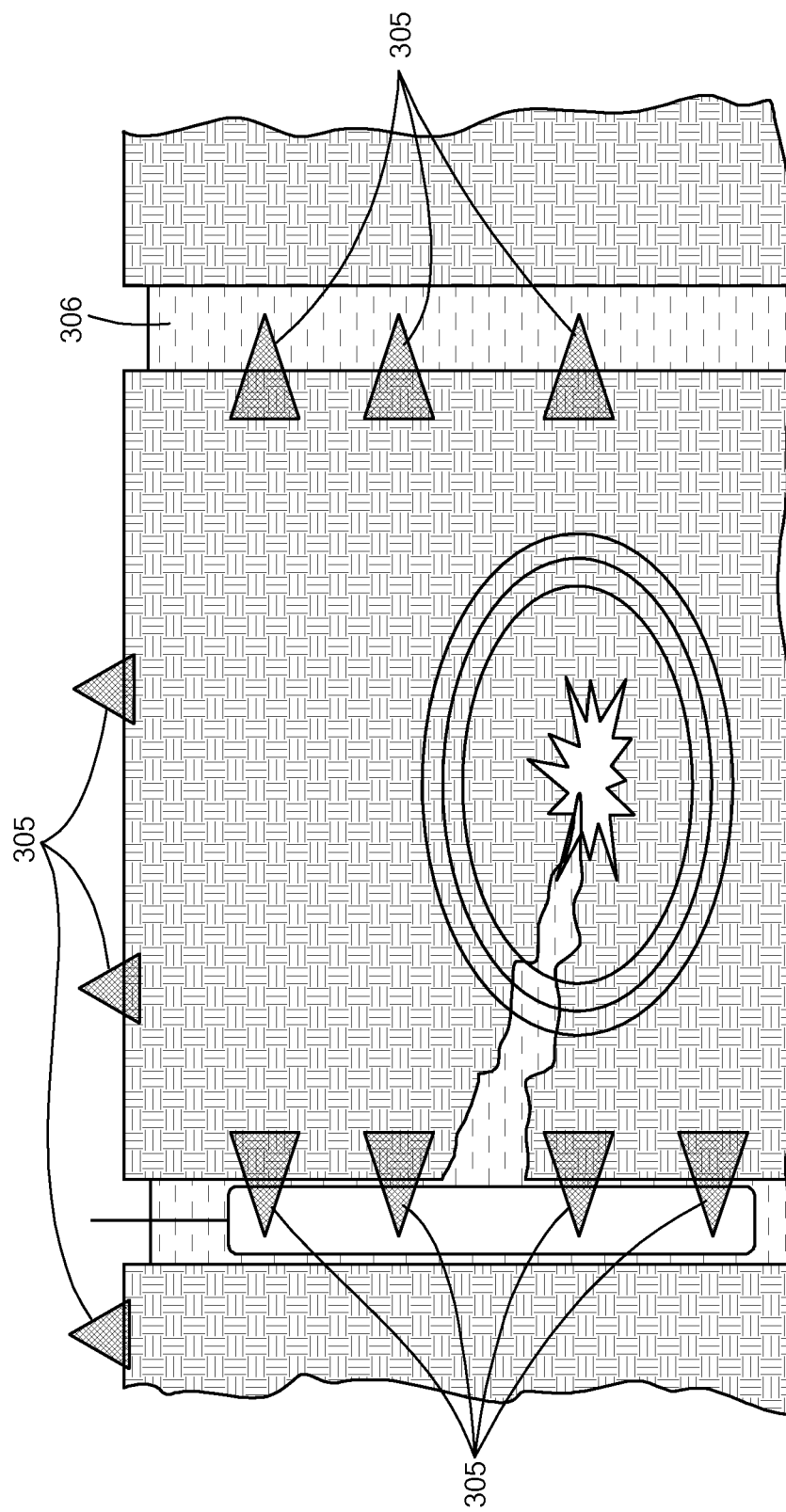

The acoustic emission for each collapse event will create an acoustic wavefront 303 which will propagate through the fluid and the surrounding rock matrix. The velocity of the wavefront will typically be equal to the sound velocity in the fluid, or in the rock matrix. By placing multiple microphones 305 at different positions in the formation, as shown, for example, in FIG. 3(b), the arrival time of the wavefronts at each microphone 305 may be determined. Based on the time delays between the arrival of the acoustic signal at the different microphones, combined with a knowledge or an educated estimation of the sound velocity in the medium, the position of the smart vessel can then be determined, using, without limitation, triangulation, similar to an underground GPS system, or using compressional/shear signal processing. The time of the sample acquisition may also be recorded. It is noted that FIG. 3(b) is by no way limited to the shown configuration of microphones or devices. In other embodiments of this invention, additional microphones may be located on the ground around the well, or at other subterranean locations, such as in a nearby well 306, cavities, or holes.

Usage as Vehicle for Time-Release of Particles, Chemical Products, or Pharmaceutical Products The above-described devices may be used as vehicles for transport and time-release of, without limitation, micro- and nano-particles, chemical and/or pharmaceutical products, by including the products or particles within the isolated cavity and/or sampling chamber separated by the mechanical structure (e.g., isolation diaphragm). The timing mechanism may trigger the piercing of the isolation diaphragm after a time delay as described above, at which point the fluid surrounding the device penetrates within the cavity behind the isolation diaphragm and comes in contact with the particles, chemical and/or pharmaceutical products. The particles or products may then dissolve within, or mix with the fluid surrounding the device, thus releasing said particles or chemical or pharmaceutical products into the surrounding environment.

Said particles or chemical products or pharmaceutical products may include, without limitation, chemicals for sanitizing water or other fluids; fluorescent chemicals that may be used as flow tracers; various chemical reagents and chemical cleaning agents; pharmaceutical products such as medications or drugs; various types of nutrients; micro- or nano-particles to be used as flow tracers; and/or chemically-functionalized micro- and nano-particles which can react to some environmental parameter.

In accordance with an embodiment of the invention, a passive timing device such as the one previously described may be injected into a geological formation or in a hydraulic fracture by means of pumping via an injection well. When the timing mechanism triggers the piercing of the isolation membrane, functionalized nanoparticles are released within the geological formation as described above. The nanoparticles react with the local environment, are carried by flow towards the injection well, and are retrieved from the well at the surface. The nanoparticle size may be chosen to be substantially smaller than the average pore throat diameter, which will insure that the particle will be transported by flow within the geological formation without clogging the pores. By analyzing the particles after retrieval at the surface, one will be able to infer information about the environment within the geological formation at the time of nanoparticle release. By injecting multiple such passive timing devices which are triggered at different times, one may be able to continuously monitor one or several parameters at multiple remote locations within the geological formation, which may be otherwise inaccessible.

FIG. 4 shows a passive timing device 404 that includes, without limitation, a pharmaceutical product 403 that is released within a human body 405, in accordance with an embodiment of the invention. The isolation diaphragm(s) is pierced at times set by the passive timing device, whereupon the corresponding pharmaceutical products 403 positioned, without limitation, within the isolated cavity and/or sampling chamber, are released within the human body. Multiple devices with one or more diaphragms may be utilized. Using such a system, complete treatment plans may be delivered without any active intervention, by adjusting the timing parameters and the types and quantities of pharmaceutical products within each cavity.

The device 404 may be attached to the skin of the human body 405, or may be implanted within the body. An external source of pressure, or an external pump, may be used to drive the timing fluid within the timing cavity of the device 404. In one embodiment, such external source of pressure may be, without limitation, a pressurized gas cartridge.

FIG. 5 shows a passive timing device that includes a filter 502 for containing the broken diaphragm particles, in accordance with an embodiment of the invention. Upon piercing of the mechanical structure (e.g., isolation diaphragm), the filter 502 advantageously prevents the broken diaphragm particles from passing into the external fluid, while still allowing, for example, a pharmaceutical product 501 to freely pass through. This embodiment may be particularly important if the passive timing device is going to be included within a human body.

Tool Implementation

The above-described devices may also be integrated within downhole sampling and measurements tools, such as the Modular Formation Dynamics Tester (MDT) produced by Schlumberger, the Formation Multi-Tester (FMT) produced by Baker Hughes or the Sequential Formation Tester (SQT) produced by Halliburton, or any other similar tool. Arrays of the sampling devices, integrating a plurality of devices and/or sampling mechanisms on a single microfabricated substrate, may be incorporated within the tool architecture. The above-described devices may also be integrated in production logging oilfield tools, possibly in slickline tools.

Figure 6:
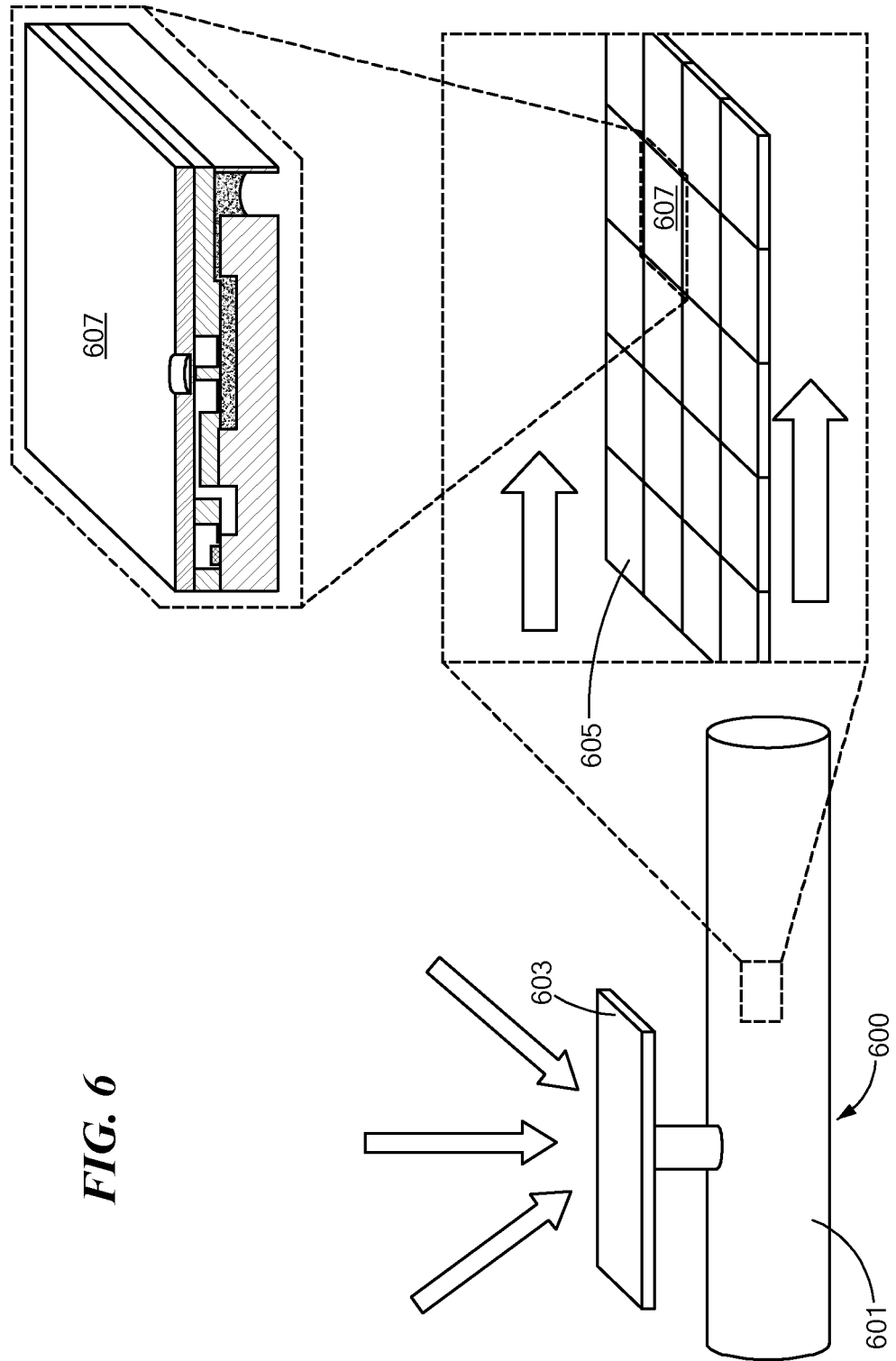
FIG. 6 shows integration of a plurality of sampling devices and/or mechanisms within an oilfield-sampling tool, in accordance with an embodiment of the invention.

FIG. 6 shows integration of a plurality of sampling devices and/or mechanisms 605 within an oilfield-sampling tool such as a MDT, a FMT or a SFT, in accordance with an embodiment of the invention. The tool 600 pushes a pad 603 into the geological formation wall, and pumps the formation fluid into an internal flow-line 601, where the fluid comes into contact with a smart sampling device array 605. Each device 607 may acquire a sample, perform a measurement, and/or emit an acoustic signal which is recorded by a microphone within the tool. The recorded acoustic signals may provide, for example, the precise time when each measurement was performed and may uniquely identify the device which performed the measurement.

The device 607 may come into contact with the formation fluid as it is pumped into the tool flowline 601. The acoustic emission events may be recorded using a microphone implemented in the tool, and later analyzed at the surface to infer the precise time of sample acquisition for each of the smart vessels in the array, thus providing very valuable time-series data.

Figure 7:
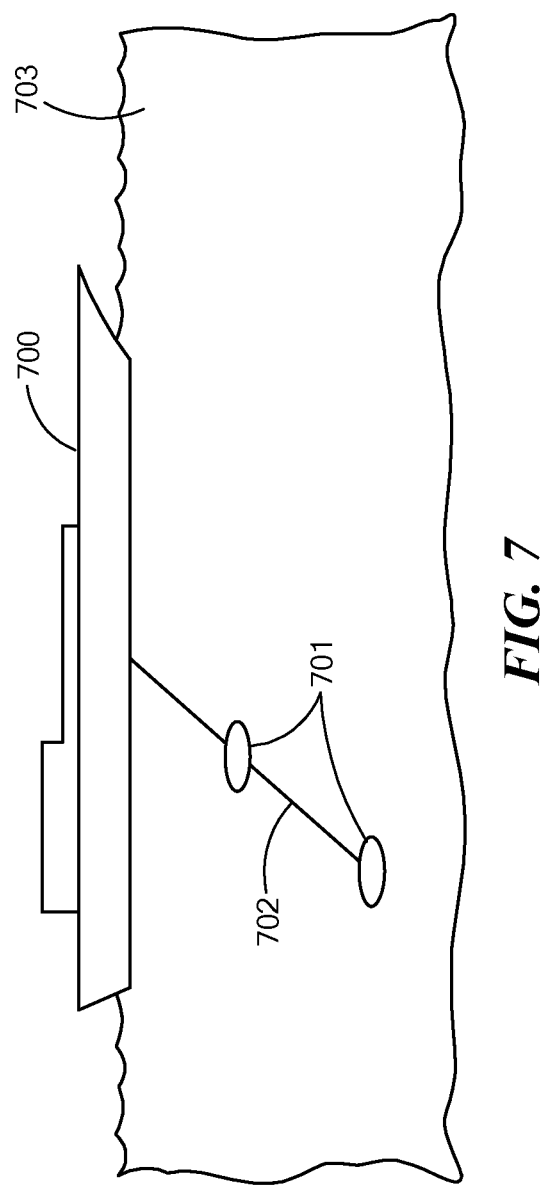
FIG. 7 shows an array of smart sampling devices embedded within an underwater measurement system which may be attached with a cable to either a buoy, a rig, a vessel or a ship, in accordance with an embodiment of the invention.

FIG. 7 shows another embodiment of the invention, where an array of smart sampling devices is embedded within a submarine measurement system 701, which may be attached with a cable 702 to, without limitation, either a buoy, a rig, a submarine, a vessel or a ship 700. The measurement system 701 may either be positioned in a stationary manner in the body of water 703, at a depth dependent, without limitation, on the length of the cable 702, or it may be dragged through the body of water by the ship 700. The smart sampling devices in the measurement system 701 perform sample acquisitions and measurements at times determined by their respective timing mechanisms, thus providing a time-series or a spatial map of measurements at a given depth.

Viscosity Measurement

FIG. 8A shows a viscosity measurement system that may be fully passive, in accordance with an embodiment of the invention. The system 801 illustratively includes two devices 805 and 806 connected together in series, in such a way that the first device's isolated cavity 802 is connected, via a conduit, such as a microfluidic channel or other type of tube of controlled dimension 803, to the timing cavity 804 of the second device. After the rupture or collapse of the first device's mechanical structure 807, the second device's timing cavity 804 will start filling with external fluid 808. The filling time of the second device's timing cavity 804, and the corresponding rupture or collapse of the second device's mechanical structure 809, may depend, at least in part, on the geometry of the conduit 803, on external pressure, and/or on the viscosity of the external fluid 808. By controlling, for example, the geometrical parameters, and by measuring external pressure, one can relate the viscosity of the external fluid to the time measured between the rupture or collapse of the first sampling device's mechanical structure 807 and that of the second device's mechanical structure 809. This allows an accurate viscosity measurement to be performed on the external fluid.

More particularly, providing that the conduit 803 has hydrodynamic resistance Rh, the external fluid has pressure P, and the timing cavity 804 has volume V, the filling time t of cavity 804 will be given by $t=Rh \times V/P$. The hydrodynamic resistance of a circular channel of radius R and length L is given by $Rh=8 \times n \times L/(\pi \times R^4)$. The hydrodynamic resistance, for a rectangular conduit of lateral dimension $h < w$ and length L, can be approximated as $Rh=12 \times n \times L/(h^3 \times w \times (1-0.63 \times h/w))$, where n is the viscosity of the external fluid (see, for example, D. Angelescu "Highly Integrated Microfluidics Design", Artech House 2011). By measuring the filling time of the cavity 804, therefore, one can infer the value of the hydrodynamic resistance of the conduit 803, and knowledge of the geometrical details of this conduit allows a determination of the fluid viscosity n from the above formulas: $n=t \times P \times \pi \times R^4/(8 \times L \times V)$ for a circular conduit, and, respectively, $n=t \times P \times h^3 \times w \times (1-0.63 \times h/w)/(12 \times L \times V)$ for a rectangular conduit.

In accordance with further related embodiments, the viscosity-measurement device described in the above paragraph may incorporate means of controlling and/or measuring the external fluid pressure, and of recording the time between the collapse of the first device's and the second device's mechanical structures 807 and 809. The collapse of a device's mechanical structure may be detected acoustically (by detecting the acoustic signature emitted during the collapse), electrically (by recording a disruption to an electrical circuit caused by the collapse), or optically (by observing the collapse using a camera, or another type of optical system), or by any other means known to a person skilled in the art.

FIG. 8B shows another embodiment of the viscosity-measurement device incorporating an additional device 810 connected in series with devices 805 and 806 in such a way that the isolated cavity of device 806 is connected to the timing cavity of the device 810 by a second conduit 811 of controlled geometry. This second conduit 811 may have different cross-section and length from the first conduit 803, thus resulting in a different timing fluid flowrate into the timing cavity 812 of the device 810.

This difference in geometry between conduits 803 and 811 may be used to extend the measurement range of a device and measure different ranges of fluid viscosity using the viscosity-measurement device. In one embodiment, the geometry of conduit 811 may be chosen so that the filling time of cavity 812 is much longer than the filling time of cavity 804 (in case we assume equal volumes for the timing cavities 804 and 812, this corresponds to the conduit 811 having significantly higher hydrodynamic resistance than conduit 803). If viscosity of the external fluid is very low, and the filling time of the cavity 804 is too short to enable an accurate measurement, then a much more accurate measurement of viscosity may be obtained by using the filling time of cavity 811. On the other hand, for highly viscous fluids, the filling time of cavity 804 may provide a reasonably accurate measurement, such that waiting for the filling of cavity 811 may no longer be necessary. Additional devices may be connected in series, with conduits connecting the isolated cavity of one device to the timing cavity of the next, to further extend the range of accurate viscosity measurements.

Manifold Sampling and Chemical/Biochemical Measurement Device

FIG. 9A shows a sampling and measurement system 901 that includes multiple devices 902, 903 connected, via a manifold 904, to an external sampling conduit 905, in accordance with an embodiment of the invention. Upon a new sample being acquired by one of the devices, new fluid may be drawn through the sampling conduit 905. The sampling chambers 906, 907 for the devices 902, 903 may be designed with volumes such that the dead volumes within the system, the internal volume of the conduit 905 or the volume of the connecting manifold 904 be negligible in comparison to the volume of the sampling chambers 906, 907.

The sampling conduit 905 may be connected to a pipe, a fluid reservoir, or another external fluid supply 908 that needs monitoring. Each time a new sample is acquired by one of the devices 902, 903, the respective volume of fluid is drawn from the said fluid supply 908, through the conduit 905 and manifold 904, into the sampling chamber of the active device.

Each sampling chamber 906, 907 may be, without limitation, a vial, a bottle and/or another leakproof container/receptacle. One or more sampling chambers 906, 907 may include a pre-measured amount of chemical or biological reagent 909, or a combination of several such reagents 910 in liquid, solid, powder or lyophilized form, in free form or immobilized on a solid substrate. Upon sample entering the sampling chamber 906, 907, a sequence of chemical or biological reactions occur between the sample and the said reagents. Different sampling chambers 906, 907 within the same system may contain different reagents 909, 910.

In various embodiments of the invention, said chemical or biological reactions may have a visible outcome. For example, the coloration of the solution or of an immobilized reagent may change, there may be a change in turbidity, there may be a development of fluorescence, or any combination of the above.

The visible outcome may be recorded in-situ, by performing an optical measurement via, without limitation, the vial wall or via an optical window 911 embedded in the sampling chamber 907. The optical measurement may include, without limitation, acquiring an image of the sampling chamber using an external optical instrument 912 such as color or black and white camera, a spectrophotometer, a fluorescence detection device, a Raman scattering device, and/or a turbidity measurement device.

FIG. 9B shows an external sampling conduit connected, via a T-junction 913, to a reagent reservoir 914, in accordance with an embodiment of the invention. The reagent reservoir 914 may be substantially at the same pressure as the fluid being sampled. For example, and without limitation, the reagent reservoir 914 may be a bladder submerged into the external fluid being sampled, or an accumulator. A fluidic resistance 915 may be included between the reagent reservoir 914 and the T-junction 913, such as to limit the flow rate of reagent. Each time a sample is drawn in, a proportional amount of reagent is drawn in along with the sample, the mixing ratio being set passively by the said fluidic resistance.

The external sampling conduit may include a micromixer 916 downstream from the T-junction 906, 907, such that the combined sample and reagent stream is thoroughly mixed after passing through the micromixer 916.

In various embodiments of the invention, the external sampling conduit may include a microfluidic sensor 917, such that each time a sample is acquired by one of the devices, the microfluidic sensor 917 performs a measurement on the fresh stream of fluid. The measurement may include, without limitation, an optical measurement (e.g., index of refraction, absorbance, fluorescence), an electrical measurement (e.g., conductivity, resistivity, dielectric constant), an electrochemical measurement (e.g., ionic content, chemical composition), a physical measurement (e.g., viscosity, density), a chemical measurement (chemical composition), and/or biological measurement (cell count).

Preconcentration and/or Sample Filtering

FIG. 10A shows a device 1001 that may be used to sample from an external fluid contaminated with one or a combination of particles 1003, organic pollutants, biological pollutants, chemical pollutants, plankton, phytoplankton, nuclear matter, volatile organic compounds, pharmaceutical matter, or other contaminants, in accordance with an embodiment of the invention. The device 1001 includes one or more integrated filters 1002 that the sample has to come in contact with, upon or prior to entering the sampling chamber 1004. The filter 1002 may include, without limitation, one or a combination of the following: a mechanical filter, a solid phase extraction column, a packed column, a hydrocarbon filter, a gas chromatography preconcentrator, a filter to collect and concentrate radioactive material, a biological filter, an absorbent medium, a scavenging medium, a hydrophobic material and a hydrophilic material.

FIG. 10B shows the device 1001 after sampling, the filter 1002 having collected different components present in the fluid sample, such as, without limitation: particles 1003, organic pollutants, biological pollutants, chemical pollutants, plankton, phytoplankton, nuclear matter, volatile organic compounds, pharmaceutical matter, or other contaminants.

The filter 1002 may, optionally, be later retrieved and analyzed, to provide time-series data concerning the contaminant of interest at the location of the device. Analyzing the filter 1002 may require backflushing, thermal desorption or solvent washing, and/or other techniques to remove the adsorbed, absorbed, or trapped contaminants. Analysis may require analytical techniques such as, without limitation, GC/MS, HPLC, gamma ray spectroscopy. In various embodiments, the filters may be analyzed in-situ.

Maintaining Sample Integrity by Controlled Sampling and High-Pressure Preservation FIGS. 11A-C shows a system 1101 capable of acquiring a sample from an external fluid 1102, pressurizing it at a pressure higher than the pressure of the external fluid, and maintaining it at such pressure for extended periods of time, in accordance with an embodiment of the invention. Such a system 1101 advantageously may ensure that the sample will remain in single-phase configuration and will not undergo a thermodynamic transition to a multi-phase fluid. This is particularly important when sampling hydrocarbon fluid from a geological formation during oilfield drilling, wireline logging, or production operations, since the sample needs to remain in single phase throughout the transport to the analysis laboratory.

The system 1101 shown in FIG. 11A includes a sampling chamber 1104 divided into a first portion and a second portion, in accordance with an embodiment of the invention. The isolated cavity of a first device 1103 is connected via a conduit to the first portion of the sampling chamber 1104. The second portion of the sampling chamber 1104 is connected via a conduit 1107 to an isolated cavity 1106 of a second device 1105. The mechanical structure 1111 of the second device 1105 may be, without limitation, scheduled to open at a later time relative to the mechanical structure 1110 of the first device 1103. The first portion of the sampling chamber 1104 may be separated from the external fluid by a first check valve 1108, allowing fluid to enter the sampling chamber 1104 but not to leave it. The connection between the two portions of the sample chamber 1104 may include a second check valve allowing flow from the second portion of the sampling chamber 1104 to the first portion of the sampling chamber 1104, but preventing flow in the opposite direction. The first and second portions of the sampling chamber 1104 may be separated by, without limitation, a leakproof piston 1109 or a flexible membrane, allowing for the pressures in the first and second portions to be equalized without requiring physical contact of the fluids in the two portions. The mechanical structure 1110 of the first device 1103 may be connected to the fluid to be sampled 1102, with the mechanical structure 1111 of the second device 1105 connected to a pressurized fluid reservoir 1112 at a pressure that is higher than the external pressure. The pressurized fluid reservoir 1112 may incorporate, without limitation, an accumulator, a pressurized gas container, and/or a mechanical spring.

FIG. 11B shows the system 1101 with the timing fluid cavity 1113 of the first device 1103 filled with timing fluid, causing the rupture or collapse of the first device's mechanical structure 1110, and allowing the external fluid 1102 to enter the first portion of the sampling chamber 1104.

FIG. 11C shows the subsequent rupture or collapse of the second device's mechanical structure 1111 (identified in FIG. 11A), the fluid from the pressurized reservoir 1112 entering the second portion of the sampling chamber 1106 and applying its pressure, via the piston 1109, to the sample contained in the first portion of the sampling chamber 1104. The fluid in the first portion of the sampling chamber 1106 is prevented from leaving the chamber by the check valve 1108, and therefore is maintained at a pressure higher than the pressure at which it was acquired.

FIG. 12A shows a device 1201 for performing a sampling operation from a high-pressure external fluid 1202 without significantly lowering the pressure of the external fluid during the sampling process (without "shocking" the fluid), in accordance with an embodiment of the invention. The sampling chamber 1203 may include a leak-proof piston 1204 or flexible membrane that separates it into a first portion 1205 and a second portion 1206. The second portion 1206, which is farther away from the mechanical structure 1210 may be pre-filled with a secondary liquid 1207 and is connected, via a conduit 1208, such as a microfluidic channel and/or fluidic constriction, to another auxiliary chamber 1209. The conduit 1208 may include a check valve 1212 or backpressure regulator that assures that the fluid 1207 does not leak from the second portion 1206 to chamber 1209 prior to sample acquisition. Upon the collapse of the mechanical structure 1210, the sample enters the first portion 1205 of sampling chamber 1203 and applies pressure to the piston 1204, which moves at a slow rate controlled, for example, by the viscosity of the secondary liquid 1207 and the geometry of the conduit 1208.

In another related embodiment, the auxiliary chamber 1209 may be pre-filled with pressurized gas. Upon sample acquisition, the gas is compressed, forming a cushion that will keep the secondary liquid 1207, and consequently the sample, pressurized. The sample in the first portion 1205 of the sampling chamber 1203 is prevented from leaving by the check valve 1211, and therefore is maintained at a pressure that is comparable to the pressure at which it was acquired.

FIG. 12B displays another embodiment of FIG. 12A that in addition to allowing a sampling operation to be performed from a high-pressure fluid without dropping the pressure of the fluid or otherwise "shocking" it during the sampling, also allows the sample to be maintained at a high pressure after sampling, possibly higher than the initial external fluid pressure, thus preventing phase separation. In addition to the details provided above with regard to FIG. 12A (the numbering of which will be maintained), in the system 1213 the second portion 1206 of the sampling chamber 1203 that is farther away from the mechanical structure 1210 is also connected via a conduit 1215 to an isolated cavity 1216 of a second device, which is scheduled to open at a later time. The conduit 1215 may include a check valve 1214 allowing flow from the isolated cavity 1216 to the second portion 1206 of the sampling chamber 1203, but preventing flow in the opposite direction. Positioned between the first portion 1205 and the second portion 1206 of the sampling chamber 1203 may be a piston or a flexible membrane allowing for the pressures to be equalized without requiring physical contact of the fluids in the two portions 1205 and 1206. The mechanical structure 1210 of the first device is connected to the fluid to be sampled 1202, whereas the mechanical structure 1217 of the second device is connected to a pressurized fluid reservoir 1218 at a pressure that is higher than the external pressure. The pressurized fluid reservoir 1218 may incorporate, without limitation, an accumulator, a pressurized gas container, and/or a mechanical spring. Upon the rupture or collapse of the first device's mechanical structure 1210, external fluid 1202 is allowed to enter the first portion 1205 of the sampling chamber 1203, at a slow rate that is controlled, at least in part, by the viscosity of the secondary liquid 1207 and/or the geometry of the conduit 1208. Upon the subsequent rupture or collapse of the second device's mechanical structure 1217, the fluid from the pressurized reservoir 1218 enters the second portion 1206 of the sampling chamber, and applies its pressure to the piston 1204, and consequently to the sample contained in the first portion 1205 of the sampling chamber 1203. The fluid in the first portion 1205 of the sampling chamber 1203 is prevented from leaving the check valve 1211, and therefore is maintained at a pressure higher than the pressure at which it was acquired.

Complex Sample Manipulations, Filter Backflushing, and Transfer Between Vials

FIGS. 13A-D show, in chronological order, operations performed by a system that, in addition to sampling at a time controlled by a passive timing mechanism, integrates a mechanism allowing the subsequent transfer of the sample from an initial sampling chamber to another sampling chamber after a given amount of time, in accordance with an embodiment of the invention. This operation can be further repeated as desired. The system described in FIGS. 13A-D may also integrate different chemical or biochemical reagents in each of the sampling chambers, and/or may integrate a filtration medium that can be backflushed as part of the sample transfer to another sampling chamber, thus concentrating certain components of the sample.

FIG. 13A shows a system 1306 that includes multiple sampling devices 1301, 1302, 1303, such that a sample from external fluid 1304 may be acquired by a first device 1301 and provided to a first portion of a sampling chamber 1305. The first portion of sampling chamber 1305 may optionally include a filter 1307. The first portion of the sampling chamber 1305 may also integrate an optional first group of chemical or biochemical reagents. The first portion of the sampling chamber 1305 may be separated from a second portion of the sampling chamber 1305 by a piston, or a flexible member membrane. The second portion of the sampling chamber 1305 is in fluidic communication with an isolated cavity 1308 of a second device 1302 that is scheduled to open at a later time. The first portion of the sampling chamber 1305 is also connected, upstream of the optional filter 1307, to the mechanical structure 1312 of a third device 1303 that is scheduled to open after the second device 1302. The mechanical structure 1313 of the second device 1302 is in turn connected to a pressurized fluid reservoir 1314, such as, without limitation, a pressurized gas reservoir, or an accumulator.

FIG. 13B shows the system 1306 after the collapse of the first device's mechanical structure 1309, showing a sample 1310 being acquired into the first portion of the sample chamber 1305, mixing with the optional first reagent of group of reagents, and pushing the piston 1311 into a far position distal the first device's mechanical structure 1309.

FIG. 13C shows the system 1306 after the later collapse of the second device's 1302 mechanical structure 1313. The pressurized fluid from reservoir 1314 enters the second device 1302 and applies its pressure to the backside of the piston 1311. The sample acquired in the first portion of the sampling chamber 1305 cannot backflow into the first device 1301 due to the check valve 1315.

FIG. 13D shows the system 1306 after the later collapse of the third mechanical structure 1312. The sample 1310 contained in the first portion of the sampling chamber 1305 is pushed, by the pressure of the pressurized gas reservoir 1314, into the sampling chamber 1315 of the third device 1303. During this process, the sample is forced to traverse the optional filter 1307 in reverse, thus back-flushing it and transporting the filtered material into the sampling chamber 1315 of the third device 1303. By choosing the volumes of the sample chamber 1315 of the third device 1303 to be lower than the volume of the first portion of sample chamber 1305, a higher concentration of the components filtered from sample 1310 can be obtained in the sampling chamber 1315. The sample chamber 1315 of the third device 1303 may also include an optional second group of chemical or biochemical reagents, such that the sample 1310, after having already reacted with the optional first group of reagents present in the first portion of the sample chamber 1305, now has to react with the optional second group of reagents. The process may be repeated multiple times.

FIG. 13E shows the above-described system 1306 slightly modified, with the sampling chamber 1305 further including a first reservoir 1316 that may be pre-filled with a liquid solution 1317, and a second reservoir 1318 that initially may be empty. The first reservoir 1316 may be separated using a piston 1319 or flexible membrane, or a similar structure, from the second portion of the sampling chamber 1305 that is in fluidic communication with the isolated cavity 1308 of the second sampling device 1302. Optionally, one-way check valves 1320, 1321 may be integrated allowing the fluid to circulate from the filter 1307 into the second reservoir 1318, and, respectively, from the first reservoir 1316 towards the filter 1307. Upon the sample acquisition by the first device 1301, the sample moves through the filter 1307 into the second reservoir 1318. Upon the collapse of the mechanical structure 1313 of the second device 1302, pressure from pressurized reservoir 1314 is applied to the liquid solution 1317 in the first reservoir 1316. As the mechanical structure 1312 of the third device 1303 collapses, the liquid solution 1317 is forced through the filter 1307, and transports the material collected on filter 1307 into the sampling chamber 1315 of the third device 1303. Optionally, a first and a second group of reagents may be incorporated in the first portion of the sampling chamber 1305, and, respectively, in the sampling chamber 1315 of the third device 1303. Additional reagents may be included in the liquid solution 1317 present in the first reservoir 1316.

The operation mode described above allows complex sample preparation, such as, without limitation, mixing with multiple chemical or biochemical reagents, backflushing using a specific liquid solution that is different from the original sample liquid, pre-concentration in a separate vial, and additional chemical and/or biochemical reactions on the preconcentrated sample.

Daisy Chain Configuration of Multiple Sampling Systems

Figure 14:
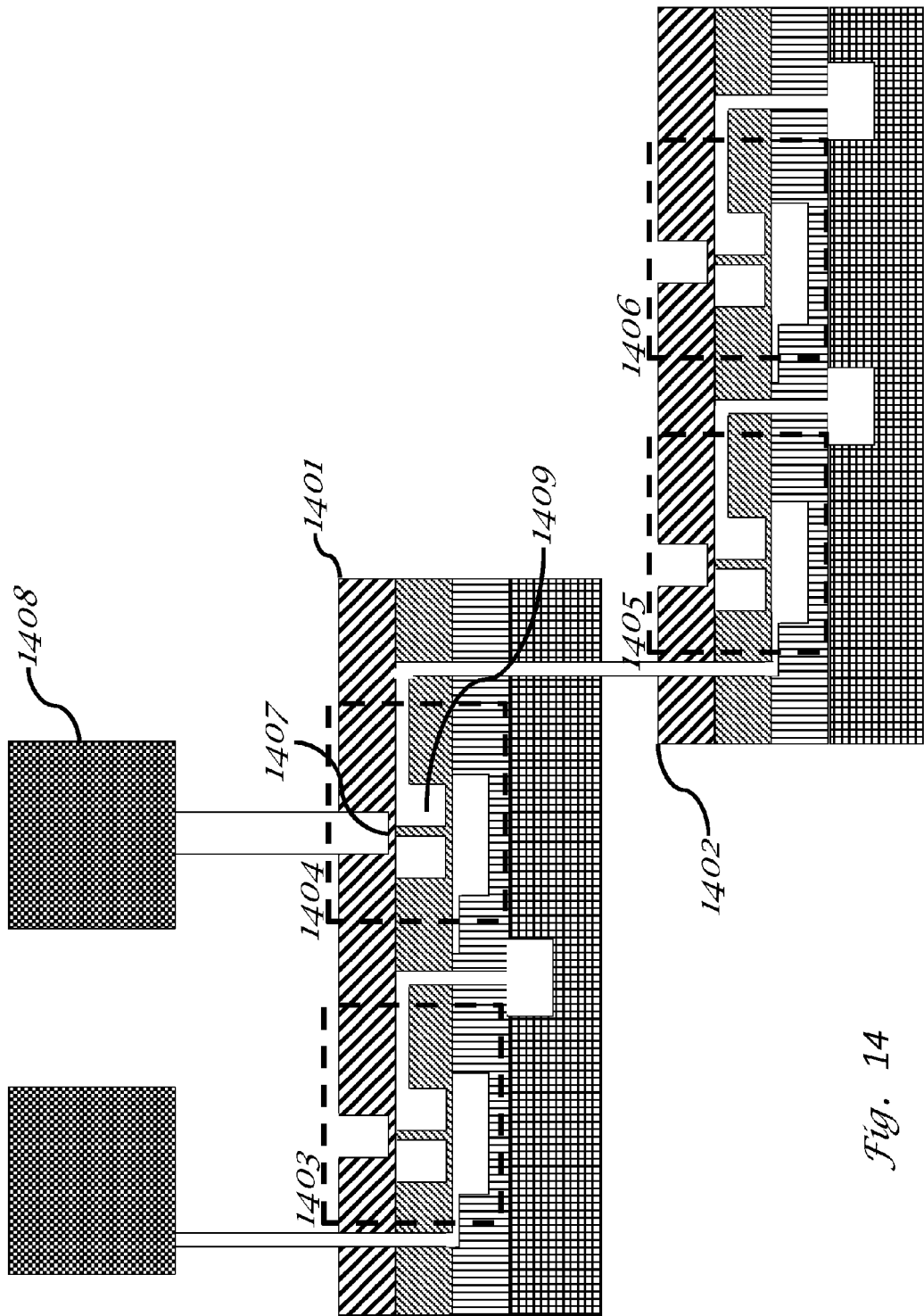
FIG. 14 shows multiple sampling systems connected in a "Daisy-chain" configuration, in accordance with an embodiment of the invention.

FIG. 14 shows multiple systems connected in a "Daisy-chain" configuration, in accordance with an embodiment of the invention. Upon one system acquiring its last sample it automatically triggers the start of sampling using the next system in the daisy chain. This mode of operation can allow an unlimited number of systems to be connected, and thus extends the sample acquisition capacity of the combined system beyond the limits of any single individual system connected in the daisy chain.

Two systems 1401 and 1402, each including a plurality of devices 1403 and 1404, and 1405 and 1406, respectively, are timed to acquire corresponding samples at different times. Illustratively, the mechanical structure 1407 of the last device 1404 of the first system 1401 may be connected to the timing fluid reservoir 1408 of the second system 1402. Additionally, the isolated cavity 1409 of the last device 1404 of the first system 1401 may be connected to the timing mechanism of one or more of the devices 1405, 1406 associated with the second system 1402. In this configuration, the collapse or rupture of the mechanical structure 1407 of the last sampling device 1404 of the first system 1401 triggers the start of the sampling using the second system 1402, thus allowing the systems to be connected in a daisy-chain configuration.

External Control of the Sampling Time

Figure 15:
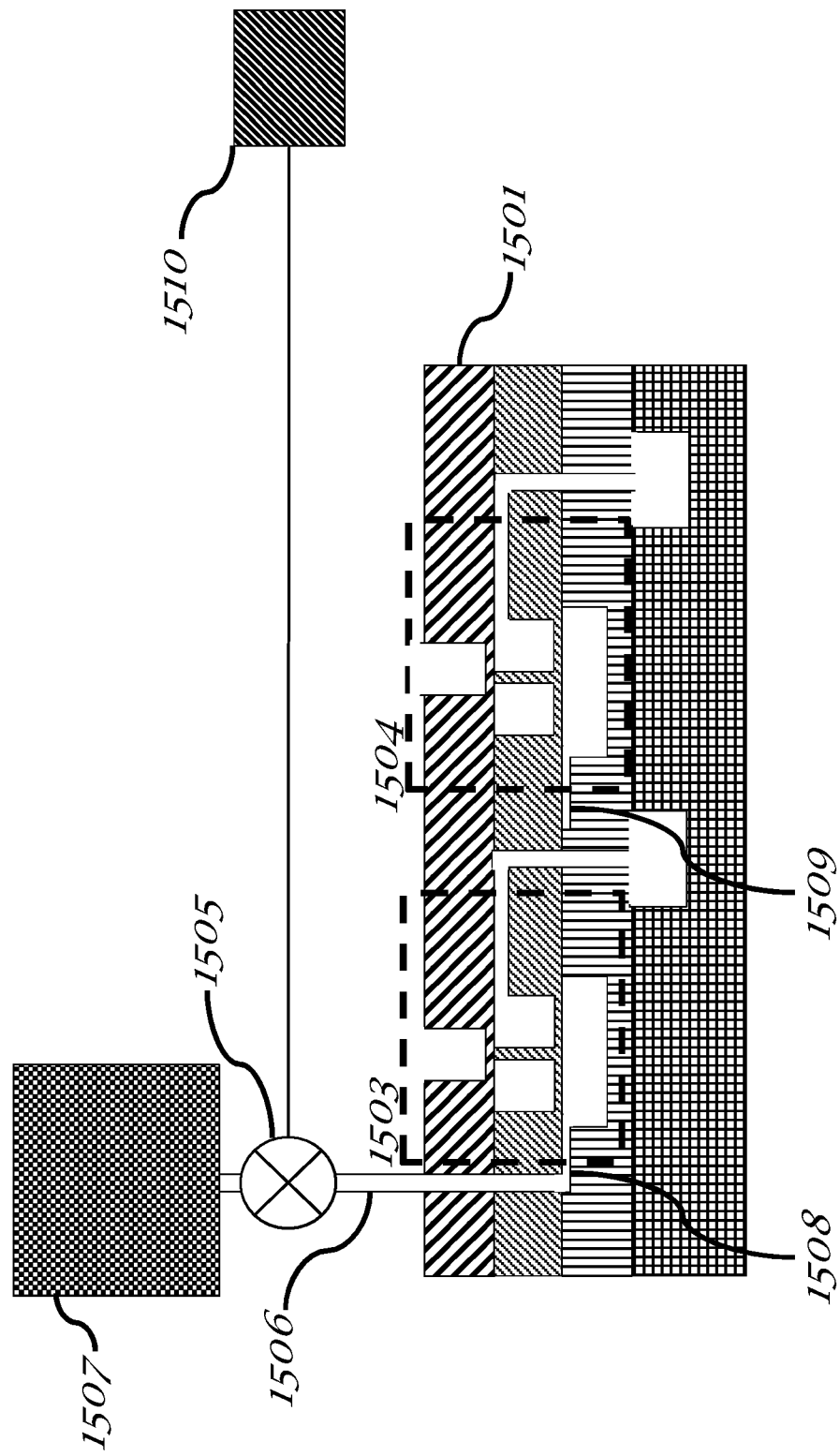
FIG. 15 shows a system capable of controlling the sampling times of a plurality of sampling devices using a trigger device, in accordance with an embodiment of the invention.

FIG. 15 shows a system 1501 capable of controlling the sampling times of a plurality of sampling devices 1503 and 1504 using a trigger device 1505 that may be in the form of a fluid control device. The trigger device 1505 may be placed, without limitation, on a timing fluid line 1506, between an optional pressurized timing fluid reservoir 1507 and the timing channels 1508, 1509 of any number of the multiple timing devices 1503, 1504 associated with the system 1501. The trigger device may be controlled by a control unit 1510 that may either be a subsystem of system 1501, or an external, possibly remote, system.

The pressurized timing fluid reservoir 1507 may be absent, instead the timing fluid may be maintained at a pressure equal to the external fluid being sampled. The trigger device 1505 can be any type of device that can enable or disable the passage of timing fluid as desired. The trigger device 1505 may be one of a check valve, an electrically-controlled solenoid valve, a fluidic switch, or any other type of active valve known in the art. The trigger device 1505 may also include a one-shot valve, that initially blocks the passage of timing fluid, and upon receipt of an external signal from the control unit 1510 permanently opens the passage of timing fluid without requiring further power.

In accordance with further embodiments, the system 1501 may incorporate a recording mechanism that records that a sample has been acquired, and/or of transmitting this information to either an external system, to the control unit 1510, or both. The collapse or rupture of the mechanical structure and the subsequent sample acquisition may be detected acoustically (by detecting the acoustic signature emitted during the collapse), electrically (by recording a disruption to an electrical circuit caused by the collapse), optically (by observing the collapse using a camera, or another type of optical system, or by observing an optical change to a vial being filled with fluid), or by any other means known in the art.

Built-in Redundancy

Due to the impracticality of on-line operation monitoring for passive devices such as the above-described devices and systems, it may be advantageous to incorporate various redundancy schemes, to minimize the chance of failure due to unforeseen circumstances. Redundant timing and sensing mechanisms, rendered possible by the extreme miniaturization may be integrated within the device. All critical device components may be built in multiple copies on a single chip, providing parallel fluid and measurement paths in case of failure (e.g., due to channel clogging or sensor malfunction). Single chips may be designed to include multiple sensor chambers for sample analysis, as well as multiple acoustic-emission isolation diaphragms and associated cavities, thus providing multiple assays and hence improved measurement statistics once the devices are recovered at the surface. Multiple timing mechanisms having different time constants may be incorporated onto a single device as well, thus providing a measurement time-series to monitor the evolution of a parameter of interest over a device well injection and retrieval cycle. The resulting device architecture can be extremely robust and should be capable of providing a reliable measurement even in the most adverse environmental conditions.

Harsh Environment Compatibility

Completely passive systems represent an advantageous approach to sensing in the very harsh environments specific to the oilfield (e.g., high temperature and pressure (HPHT), corrosive fluids, severely constrained geometry). The above-described embodiments allow the deployment of smart passive devices that are capable of performing a number of specific, well-defined functions in, without limitation, the subterranean environment surrounding an oil well, without requiring power, monitoring, or telemetry. Such smart passive devices can be deployed downhole by pumping along with frac- or other injected fluids, or they can be integrated within existing oilfield measurement tools such as the MDT tool, the FMT tool or the SFT tool. The smart devices may acquire, react with, and isolate a sample of downhole fluid, and, once retrieved from the reservoir, they can be interrogated by optical, electrical or other means to provide information about the environment they have been exposed to (e.g. chemical or physical properties of the fluids encountered) as well as about the times when the measurements were performed. Additionally, as described above, the device can emit bursts of acoustic signals at pre-defined times which can allow device localization by, without limitation, triangulation using multiple microphones.

All the device functionalities recited above may be implemented in multiple applications, and are not limited in any way to oilfield measurements. Examples of different applications include, but are in no way limited to: submarine deployment of such systems as in a body of water, river, lake, sea, ocean; measurements within water wells and aquifers; waste water storage tanks and reservoirs, and the monitoring thereof; and injection wells for carbone dioxide sequestration.

The above-described embodiments are not constrained to a specific sensing technology—several technologies are compatible with and can be integrated within such a smart passive device, such as, without limitation: purely chemical sensors (e.g. titration reactions), corrosion sensors, MEMS sensors, electrochemical sensors, and functionalized nanoparticles. The purely passive devices may be mission-specific so as to integrate only those functions that are absolutely paramount to performing and later interpreting the specific measurement (or chemical reaction) of interest; all additional functionality will be provided externally after recovery. This purely passive approach therefore minimizes the risk of system failure due to environmental issues.

Ultimate Size Miniaturization

Besides the capability to survive a harsh environment, a fully passive system provides ultimate miniaturization capabilities. Typically, physical transducers occupy only a very small percentage of the total package size in miniaturized sensors (such as those using MEMS technology), the rest being occupied by electronics and connections. A passive approach eliminates the need to operate electronics downhole, and thus can lead to impressive size reduction. The use of small, passive devices, that may be fabricated using, without limitation, MEMS technology, permits deployment within pores and/or fractures of the rock. Such deployment may be performed, for example, as part of a proppant formulation during hydraulic fracturing operations.

In summary, the above-described devices enable a variety of functionalities. These functionalities include, without limitation, the following:

1. mechanical protection and hermetic transport of the device within the external environment (by pumping or injection), or deployment within various measurement tools;

2. sample acquisition, material release and/or chemical reaction in-situ at pre-defined times, using passive microfluidic timing mechanisms;

3. sample isolation from external medium prior to and after acquisition (cross-contamination control);

4. integrated redundancy mechanisms to assure correct device operation even in cases of failure of one of the sample mechanisms;

5. monolythic integration with standard sensor technologies;

6. three-dimensional positioning using coded and/or uncoded acoustic signal emission;

7. external sensor interrogation capability after retrieval at the surface;

8. filtering 9. measuring viscosity of an external fluid;

10. maintaining a sample at high pressure after sample acquisition, to ensure sample integrity and single-phase character;

11. complex sample manipulations, filter backflushing, and transfer between vials;

12. manifold sampling and chemical/biochemical measurement;

13. daisy chain configuration of multiple sampling systems; and 14. external control of sampling time.

The above-described devices provide robust, highly miniaturized smart passive sample chambers/vessels that can be integrated with several sensor technologies to perform critical in-situ measurements for, without limitation, the oilfield or a living body, or to provide information about the positioning of devices during fluid injection or fracturing operations. One of the main features of the device is its capability to provide a robust timing mechanism to perform, for example, measurements or material release on a pre-defined (or post-inferred) schedule, and/or to emit acoustic signal sequences, which will allow triangulation of the vessel position, thus indicating fluid movement and fracture propagation, within a hydrocarbon reservoir, or other pressurized formation or system. From fracture propagation modeling relative to induced pressures, formation mechanical properties and stress analysis can be performed in-situ. The device may be integrated with standard sensing technologies, allowing a specific measurement or set of measurements to be performed on an isolated fluid sample. The device may also be utilized as part of a proppant formulation during hydraulic fracturing jobs, whereas the passive devices are mixed with slurries and sand grains and are injected alongside into a formation. The device may be used to as a vehicle for time-release of particles, chemical products, or pharmaceutical products. The device may be used in autonomous devices, for example, on robots such as marine remotely-operated underwater vehicles, autonomous underwater vehicles, airborne or ground drones and vehicles, and other types of robotic equipment. The device may be used to monitor flow of external fluids/gases in and around, without limitation, cities, chemical plants, nuclear sites, remote regions without power, offshore platforms and other oilfield structures, military missions and battlegrounds.

These combined capabilities result, without limitation, in a very versatile device capable of being implemented within a tool or injected in a formation or living body, to provide measurements on samples acquired and/or to release particles, at different locations in, without limitation, an oil reservoir or body and at multiple times, and to communicate its position via acoustic emission.

The embodiments of the invention described above are intended to be merely exemplary; numerous variations and modifications will be apparent to those skilled in the art. All such variations and modifications are intended to be within the scope of the present invention. These and other obvious modifications are intended to be covered by the claims that follow.

What is claimed is:

1. A system comprising:
one or more devices; each device including:
an isolated cavity that is initially inaccessible to an external fluid;
an electrically passive timing mechanism; and
a mechanical structure separating the isolated cavity from the exterior environment, such that at the end of a timing interval the timing mechanism acts on the mechanical structure to rupture and/or collapse the mechanical structure, thus bringing the isolated cavity in contact with the external fluid, wherein the mechanical structure is made of a material selected from the group consisting of an inorganic material, a non-polymeric material, silicon, glass, ceramic and combinations thereof.

2. The system according to claim 1, wherein the isolated cavity is in fluidic communication with a sampling chamber.

3. The system according to claim 2, further including a one-way check valve between the isolated cavity and the sampling chamber that allows fluid flow into the sampling chamber.

4. The system according to claim 2, wherein the sampling chamber includes one or more chemical and/or biological reagents.

5. The system according to claim 2, further comprising a filter for filtering fluid upon or prior to entering the sampling chamber.

6. The system according to claim 5, wherein the filter is selected from the group consisting of a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, a hydrophilic material, and combination thereof.

7. The system according to claim 3, wherein the sampling chamber of a first device of the one or more devices includes a piston and/or a flexible membrane that separates the sampling chamber into a first portion and a second portion, the first portion in fluidic communication with the isolated cavity.

8. The system according to claim 7, wherein the second portion is in fluidic communication with an auxiliary chamber via a conduit, wherein the second portion is initially filled with a secondary liquid, and wherein upon rupture and/or collapse of the mechanical structure, fluid from the external environment enters the sampling chamber and applies pressure to the piston, which moves at a rate based, at least in part, on the value of the pressure of the external fluid, the viscosity of the secondary liquid and/or the geometry of said conduit.

9. The system according to claim 7, wherein the one or more devices include a second device,
wherein the mechanical structure of the second device separates the isolated cavity of the second device from a pressurized fluid,
wherein the isolated cavity of the second device is in fluidic communication with the second portion of the sampling chamber, such that at the end of a timing interval the timing mechanism of the second device acts on the mechanical structure of the second device to rupture and/or collapse the mechanical structure of the second device, thus bringing the isolated cavity of the second device and the second portion of the sample chamber in fluidic communication with the pressurized fluid,
and wherein the timing mechanisms of the first and second device are configured such that the mechanical structure of the second device ruptures and/or collapses after the mechanical structure of the first device ruptures and/or collapses.

10. The system according to claim 1, wherein the passive timing mechanism includes:
a timing diaphragm;
a timing cavity; and
a conduit in fluidic communication with the timing cavity, such that upon applying pressure to a timing fluid within the conduit, said timing fluid advances within the conduit and upon reaching the timing cavity and filling it after a timing interval, the timing fluid applies pressure to the timing diaphragm which ruptures and/or collapses the mechanical structure thus allowing external fluid to enter the isolated cavity.

11. The system according to claim 10, the one or more devices including a first and second device, wherein the isolated cavity of the first device is coupled to the timing cavity of the second device via a conduit, and wherein upon rupture and/or collapse of the mechanical structure of the first device, external fluid enters the isolated cavity of the first device and further communicates with the timing cavity of the second device such that the external fluid acts as the timing fluid for the second device, and such that the timing cavity of the second device fills and the external fluid pressure is applied to the timing diaphragm of the second device causing the mechanical structure of the second device to collapse and/or rupture.

12. The system according to claim 11, further including a controller configured to determine viscosity of the external fluid based on, at least in part, a measurement associated with the time of rupture and/or collapse of the one or more devices.

13. The system according to claim 11, further comprising a third device, the isolated cavity of the second device in fluidic communication with the timing mechanism of the third device, wherein the timing mechanisms of the second and third devices differ.

14. The system according to claim 1, further including:
a triggering mechanism configured to turn on and/or off the timing mechanism of at least one of the devices upon an external command.

15. The system according to claim 14, wherein the triggering mechanism includes a component selected from a check valve, a solenoid valve, a one-shot valve, a fluidic switch, a MEMS component, a detonator, and any combination thereof.

16. The system according to claim 1, wherein the external fluid of the one or more devices differ.

17. The system according to claim 1, wherein at least one of the one or more devices includes a releasable weight upon acquisition of the external fluid.

18. A system comprising:
one or more devices; each device including:
an isolated cavity that is initially inaccessible to an external fluid;
an electrically passive timing mechanism; and
a mechanical structure separating the isolated cavity from the exterior environment, such that at the end of a timing interval the timing mechanism acts on the mechanical structure to rupture and/or collapse the mechanical structure, thus bringing the isolated cavity in contact with the external fluid, wherein the mechanical structure is insoluble in a liquid selected from the group consisting of water, bodily fluids, oil, oil field fluid, crude oil, salt water, sea water and combinations thereof.

19. The system according to claim 18, wherein the isolated cavity is in fluidic communication with a sampling chamber.

20. The system according to claim 19, further including a one-way check valve between the isolated cavity and the sampling chamber that allows fluid flow into the sampling chamber.

21. The system according to claim 19, wherein the sampling chamber includes one or more chemical and/or biological reagents.

22. The system according to claim 19, further comprising a filter for filtering fluid upon or prior to entering the sampling chamber.

23. The system according to claim 22, wherein the filter is selected from the group consisting of a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, a hydrophilic material, and combination thereof.

24. The system according to claim 20, wherein the sampling chamber of a first device of the one or more devices includes a piston and/or a flexible membrane that separates the sampling chamber into a first portion and a second portion, the first portion in fluidic communication with the isolated cavity.

25. The system according to claim 24, wherein the second portion is in fluidic communication with an auxiliary chamber via a conduit, wherein the second portion is initially filled with a secondary liquid, and wherein upon rupture and/or collapse of the mechanical structure, fluid from the external environment enters the sampling chamber and applies pressure to the piston, which moves at a rate based, at least in part, on the value of the pressure of the external fluid, the viscosity of the secondary liquid and/or the geometry of said conduit.

26. The system according to claim 24, wherein the one or more devices include a second device,
wherein the mechanical structure of the second device separates the isolated cavity of the second device from a pressurized fluid,
wherein the isolated cavity of the second device is in fluidic communication with the second portion of the sampling chamber, such that at the end of a timing interval the timing mechanism of the second device acts on the mechanical structure of the second device to rupture and/or collapse the mechanical structure of the second device, thus bringing the isolated cavity of the second device and the second portion of the sample chamber in fluidic communication with the pressurized fluid,
and wherein the timing mechanisms of the first and second device are configured such that the mechanical structure of the second device ruptures and/or collapses after the mechanical structure of the first device ruptures and/or collapses.

27. The system according to claim 18, wherein the passive timing mechanism includes:
a timing diaphragm;
a timing cavity; and
a conduit in fluidic communication with the timing cavity, such that upon applying pressure to a timing fluid within the conduit, said timing fluid advances within the conduit and upon reaching the timing cavity and filling it after a timing interval, the timing fluid applies pressure to the timing diaphragm which ruptures and/or collapses the mechanical structure thus allowing external fluid to enter the isolated cavity.

28. The system according to claim 27, the one or more devices including a first and second device, wherein the isolated cavity of the first device is coupled to the timing cavity of the second device via a conduit, and wherein upon rupture and/or collapse of the mechanical structure of the first device, external fluid enters the isolated cavity of the first device and further communicates with the timing cavity of the second device such that the external fluid acts as the timing fluid for the second device, and such that the timing cavity of the second device fills and the external fluid pressure is applied to the timing diaphragm of the second device causing the mechanical structure of the second device to collapse and/or rupture.

29. The system according to claim 28, further including a controller configured to determine viscosity of the external fluid based on, at least in part, a measurement associated with the time of rupture and/or collapse of the one or more devices.

30. The system according to claim 28, further comprising a third device, the isolated cavity of the second device in fluidic communication with the timing mechanism of the third device, wherein the timing mechanisms of the second and third devices differ.

31. The system according to claim 18, further including:
a triggering mechanism configured to turn on and/or off the timing mechanism of at least one of the devices upon an external command.

32. The system according to claim 31, wherein the triggering mechanism includes a component selected from a check valve, a solenoid valve, a one-shot valve, a fluidic switch, a MEMS component, a detonator, and any combination thereof.

33. The system according to claim 18, wherein the external fluid of the one or more devices differ.

34. The system according to claim 18, wherein at least one of the one or more devices includes a releasable weight upon acquisition of the external fluid.

35. A method for determining viscosity of an external fluid, the method comprising:
deploying a system in an external fluid, the system including a plurality of devices;
opening an isolated cavity of a first device, at a time determined by an electrically passive timing mechanism of the first device, such that the external fluid enters the isolated cavity of the first device, the isolated cavity of the first device in fluidic communication with a timing mechanism of the second device;

opening an isolated cavity of a second device, at a time determined, at least in part, by the timing mechanism of the second device and the viscosity of the external fluid; and determining viscosity of the external fluid based on, at least in part, a measurement associated with the opening of the isolated cavities of the first and second devices.

36. The method according to claim 35, wherein the passive timing mechanism of each device includes:
   a timing diaphragm;
   a timing cavity; and a conduit in fluidic communication with the timing cavity, such that upon applying pressure to a timing fluid within the conduit, said timing fluid advances within the conduit and upon reaching the timing cavity and filling it after a timing interval, the timing fluid applies pressure to the timing diaphragm which ruptures and/or collapses the mechanical structure thus allowing external fluid to enter the isolated cavity.

37. The method according to claim 35, further comprising a third device, the isolated cavity of the second device in fluidic communication with a timing mechanism of the third device, the method further comprising:
   opening an isolated cavity of the third device, at a time determined, at least in part, by the timing mechanism of the third device and by the viscosity of the external fluid, wherein the timing mechanisms of the second and third devices differ,
   wherein determining viscosity of the external fluid is based on, at least in part, a measurement associated with the opening of the isolated cavities of the first, second and third devices.

38. A system comprising:
   one or more devices; each device including:
      an isolated cavity that is initially inaccessible to an external fluid;
      an electrically passive timing mechanism; and
      a mechanical structure separating the isolated cavity from the exterior environment, such that at the end of a timing interval the timing mechanism acts on the mechanical structure to rupture and/or collapse the mechanical structure, thus bringing the isolated cavity in contact with the external fluid, wherein the isolated cavity is in fluidic communication with a sampling chamber.

39. The system according to claim 38, further including a one-way check valve between the isolated cavity and the sampling chamber that allows fluid flow into the sampling chamber.

40. The system according to claim 38, wherein the sampling chamber includes one or more chemical and/or biological reagents.

41. The system according to claim 38, further comprising a filter for filtering fluid upon or prior to entering the sampling chamber.

42. The system according to claim 41, wherein the filter is selected from the group consisting of a mechanical filter, a solid phase extraction column, a hydrocarbon filter, a gas chromatography preconcentrator, a packed column, a filter that collects and concentrates radioactive material, a biological filter, an absorbent medium, a scavenging medium, a hydrophobic material, a hydrophilic material, and combination thereof.

43. The system according to claim 39, wherein the sampling chamber of a first device of the one or more devices includes a piston and/or a flexible membrane that separates the sampling chamber into a first portion and a second portion, the first portion in fluidic communication with the isolated cavity.

44. The system according to claim 43, wherein the second portion is in fluidic communication with an auxiliary chamber via a conduit, wherein the second portion is initially filled with a secondary liquid, and wherein upon rupture and/or collapse of the mechanical structure, fluid from the external environment enters the sampling chamber and applies pressure to the piston, which moves at a rate based, at least in part, on the value of the pressure of the external fluid, the viscosity of the secondary liquid and/or the geometry of said conduit.

45. The system according to claim 43, wherein the one or more devices include a second device,
   wherein the mechanical structure of the second device separates the isolated cavity of the second device from a pressurized fluid,
   wherein the isolated cavity of the second device is in fluidic communication with the second portion of the sampling chamber, such that at the end of a timing interval the timing mechanism of the second device acts on the mechanical structure of the second device to rupture and/or collapse the mechanical structure of the second device, thus bringing the isolated cavity of the second device and the second portion of the sample chamber in fluidic communication with the pressurized fluid,
   and wherein the timing mechanisms of the first and second device are configured such that the mechanical structure of the second device ruptures and/or collapses after the mechanical structure of the first device ruptures and/or collapses.

46. The system according to claim 45, wherein the one or more devices includes a third device having a mechanical structure in fluidic communication with the first portion of the sampling chamber, such that rupture and/or collapse of the mechanical structure of the third device allows fluid communication between the first portion of the sampling chamber and a second sampling chamber,
   and wherein the timing mechanism of the third device is configured such that the mechanical structure of the third device ruptures and/or collapses after the mechanical structure of the second device ruptures and/or collapses.

47. The system according to claim 46, wherein the first portion of the sampling chamber includes a filter for retaining certain components from fluid entering the sampling chamber, the filter positioned within the sampling chamber such that fluid flowing between the sampling chamber and the second sampling chamber transports the retained components.

48. The system according to claim 47, further including:
   a first reservoir between the piston and the first portion of the sampling chamber, the first reservoir filled with a fluid and/or a reagent solution in fluidic communication with the first portion, such that fluid can flow from the first reservoir to the first portion of the sampling chamber, and
   a second reservoir in fluidic communication with the first portion of sampling chamber, the second reservoir for receiving overflow from the first portion of the sampling chamber, wherein upon the collapse and/or rupture of the third devices mechanical structure, the fluid and/or reagent solution from the first reservoir flows through the filter and into the second sampling chamber.

49. The system according to claim 38, further comprising:
a manifold, the manifold in fluidic communication with the isolated cavity of each device upon rupture and/or collapse of their associated mechanical structure; and
a sampling conduit in fluidic communication with the manifold and the external fluid.

50. The system according to claim 49, wherein the sampling conduit is further in communication with a reagent reservoir that holds a reagent.

51. The system according to claim 50, further comprising a mechanism selected from the group consisting of a mixer for mixing the reagent and the external fluid, a sensor for performing measurements on fluid with the sampling conduit, and combination therein.

52. The system according to claim 38, further comprising a first and a second group of the one or more devices, wherein the isolated chamber of one of the devices in the first group of devices is coupled to the timing mechanism of each of the devices in the second group such that the mechanical structures of the second group rupture and/or collapse after the mechanical structure of the one of the devices.

53. The system according to claim 38, further including:
a triggering mechanism configured to turn on and/or off the timing mechanism of at least one of the devices upon an external command.

54. The system according to claim 53, wherein the triggering mechanism includes a component selected from a check valve, a solenoid valve, a one-shot valve, a fluidic switch, a MEMS component, a detonator, and any combination thereof.

55. The system according to claim 38, wherein the external fluid of the one or more devices differ.

56. The system according to claim 38, wherein at least one of the one or more devices includes a releasable weight upon acquisition of the external fluid.

* * * * *